US008219417B2

(12) United States Patent　(10) Patent No.: US 8,219,417 B2
Dalton　(45) Date of Patent: *Jul. 10, 2012

(54) FRONT END

(75) Inventor: William S. Dalton, Temple Terrace, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 48 days.

This patent is subject to a terminal disclaimer.

(21) Appl. No.: 13/022,464

(22) Filed: Feb. 7, 2011

(65) Prior Publication Data

US 2011/0276339 A1　Nov. 10, 2011

Related U.S. Application Data

(62) Division of application No. 10/846,977, filed on May 14, 2004, now Pat. No. 8,135,595.

(51) Int. Cl.
*G06Q 10/00* (2012.01)
*G06Q 40/00* (2012.01)
*G06Q 50/00* (2012.01)

(52) U.S. Cl. .................................... 705/2; 705/3; 705/4
(58) Field of Classification Search .................. 705/2, 3, 705/4

See application file for complete search history.

(56) References Cited

U.S. PATENT DOCUMENTS

| 4,132,769 | A | * | 1/1979 | Osther ........................ 424/174.1 |
| 5,075,217 | A | | 12/1991 | Weber |
| 5,324,631 | A | | 6/1994 | Helentjaris et al. |
| 5,510,270 | A | | 4/1996 | Fodor et al. |
| 5,539,083 | A | | 7/1996 | Cook et al. |
| 5,545,522 | A | | 8/1996 | Van Gelder et al. |
| 5,556,752 | A | | 9/1996 | Lockhart et al. |
| 5,578,832 | A | | 11/1996 | Trulson et al. |
| 5,594,638 | A | * | 1/1997 | Iliff ................................. 705/3 |
| 5,716,785 | A | | 2/1998 | Van Gelder et al. |
| 5,891,636 | A | | 4/1999 | Van Gelder et al. |
| 6,028,189 | A | | 2/2000 | Blanchard |
| 6,132,997 | A | | 10/2000 | Shannon |
| 6,188,988 | B1 | * | 2/2001 | Barry et al. ....................... 705/3 |
| 6,271,002 | B1 | | 8/2001 | Linsley et al. |
| 6,553,317 | B1 | | 4/2003 | Lincoln et al. |
| 6,572,564 | B2 | | 6/2003 | Ito et al. |

(Continued)

FOREIGN PATENT DOCUMENTS

EP　0 534 858　3/1993

(Continued)

OTHER PUBLICATIONS

Google search, "define: longitudinal study" [retrieved on Nov. 2, 2011]; retrieved from the Internet URL: http://www.etr.org/.

(Continued)

*Primary Examiner* — Neal Sereboff
(74) *Attorney, Agent, or Firm* — Fish & Richardson P.C.

(57) ABSTRACT

Systems and methods are provided including a system for managing patient data. The system includes a computing system including a processing unit and a storage. The processing unit executes one or more programs for managing patient data. Managing patient data includes enrolling patients in a centralized care network including presenting each patient with an electronic enrollment interface, assigning each patient a patient identifier, and receiving an electronic consent to collect data. Managing patient data further includes providing patient data to the centralized care network including patient data relating to disease progression, clinical trials and treatments rendered.

8 Claims, 8 Drawing Sheets

U.S. PATENT DOCUMENTS

| | | | |
|---|---|---|---|
| 6,741,976 | B1 | 5/2004 | Tuzhiliin |
| 2001/0034023 | A1* | 10/2001 | Stanton et al. .................... 435/6 |
| 2002/0076735 | A1* | 6/2002 | Williams et al. ............. 435/7.23 |
| 2002/0150966 | A1* | 10/2002 | Muraca ........................ 435/40.5 |
| 2002/0179097 | A1 | 12/2002 | Atkins |
| 2003/0027223 | A1 | 2/2003 | Muraca |
| 2003/0036683 | A1* | 2/2003 | Kehr et al. .................... 600/300 |
| 2003/0046110 | A1 | 3/2003 | Gogolak |
| 2003/0163348 | A1 | 8/2003 | Stead et al. |
| 2003/0219774 | A1* | 11/2003 | Sharma et al. .................... 435/6 |
| 2003/0224467 | A1* | 12/2003 | Osborne et al. ............. 435/7.23 |
| 2003/0229517 | A1 | 12/2003 | Meserol et al. |
| 2004/0006492 | A1 | 1/2004 | Watanabe |
| 2004/0013663 | A1* | 1/2004 | Choong-Chin et al. ... 424/130.1 |
| 2004/0015337 | A1* | 1/2004 | Thomas et al. ................. 703/11 |
| 2004/0121350 | A1* | 6/2004 | Anderberg et al. ............... 435/6 |
| 2004/0122709 | A1* | 6/2004 | Avinash et al. ................... 705/2 |
| 2004/0158408 | A1 | 8/2004 | Choi et al. |
| 2004/0193019 | A1* | 9/2004 | Wei ............................... 600/300 |
| 2004/0221855 | A1* | 11/2004 | Ashton ......................... 128/898 |
| 2004/0234988 | A1 | 11/2004 | Oka et al. |
| 2005/0069863 | A1* | 3/2005 | Moraleda et al. ................. 435/4 |
| 2005/0071087 | A1* | 3/2005 | Anderson ...................... 702/19 |
| 2005/0071143 | A1* | 3/2005 | Tran et al. ...................... 703/11 |
| 2006/0121452 | A1* | 6/2006 | Dhallan ........................... 435/5 |

FOREIGN PATENT DOCUMENTS

| | | |
|---|---|---|
| WO | WO 98/41531 | 9/1998 |

OTHER PUBLICATIONS

American Cancer Society, Inc., 2003, "Cancer Facts & Figures 2003," 52 pages.

Amos et al., 1990, "A multivariate method for detecting genetic linkage, with application to a pedigree with an adverse lipoprotein phenotype," Am. J. Hum. Genet. 47:247-254.

Agrawal et al., 2002, "Osteopontin Identified as Lead Marker of Colon Cancer Progression, Using Pooled Sample Expression Profiling," Journal of the National Cancer Institute 94:513-520.

Armstrong et al., 2002, "*MLL* translocations specify a distinct gene expression profile that distinguishes a unique leukemia," Nature Genetics 30:41-47.

Bates et al., 2003, "A Proposal for Electronic Medical Records in U.S. Primary Care," Journal of the American Medical Informatics Association 10:1-10.

Bates et al., 2001, "Reducing the Frequency of Errors in Medicine Using Information Technology," Journal of the American Medical Informatics Association 8:299-308.

Bates et al., 1999, "The Impact of Computerized Physician Order Entry on Medication Error Prevention," Journal of the American Medical Informatics Association 6:313-321.

Blanchard et al., 1996, "Sequence to array: Probing the genome's secrets," Nature Biotechnology 14:1649.

Bochner et al., 2001, "Phenotype microarrays for high-throughput phenotypic testing and assay of gene function," Genome Res. 11:1246-1255.

Brown et al., 2000, "Knowledge-based analysis of microarray gene expression data by using support vector machines," Proc. Natl. Acad. Sci. USA 97:262-267.

Breitfeld et al., 1999, "Pilot Study of a Point-of-use Decision Support Tool for Cancer Clinical Trials Eligibility," Journal of the American Medical Informatics Association 6:467-477.

Cohen et al., 2000, "A computational analysis of whole-genome expression data reveals chromosomal domains of gene expression," Nature Genetics 26:183-186.

Dalton, "Portrait of a World-Class Cancer Center," Mar. 12, 2004, slides accompanying Grand Rounds powerpoint presentation, 39 pp.

Dalton, "Portrait of a World-Class Cancer Center," DVD of Grand Rapids Presentation, Mar. 12, 2004.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Drăghici, 2003, *Data Analysis Tools for DNA Microarrays*, Chapman & Hall/CRC, London, U.K.

Duda et al., 2001, *Pattern Classification*, John Wiley & Sons, New York, NY, p. 521-530.

Duda et al., 2001, *Pattern Classification*, John Wiley & Sons, New York, NY, p. 550-557.

Easton et al., 1993, "Inherited susceptibility to breast cancer," Cancer Surv. 18:95-113.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fodor et al., 1991, "Light-directed, spatially addressable parallel chemical synthesis," Science 251:767-773.

Gaasterland et al., 2000, "Making the most of microarray data," Nature Genetics 24:204-206.

General Practitioners Committee, 2003, "Good practice guidelines for general practice electronic patient records (version 3)," Department of Health & Royal College of General Practitioners, 74 pages.

Genomic Health—Future Directions, 2004, "Developing state of the art genomic technologies," http://www.genomichealth.com/future/defalut.aspx.

Genomic Health, 2004, "Pioneering a new era of cancer care," http://www.genomichealth.com.

Genomic Health—About Genomic Health, 2004, "Improving the quality of treatment decisions," http://www.genomichealth.com/about/default.aspx.

Genomic Health, 2004, "Applying Genomics to Cancer," http://www.genomichealth.com/genomics/applying.aspx.

Genomic Health, 2004, "Understanding Genomics," http://www.genomichealth.com/genomics/understanding.aspx.

Genomic Health, 2004, "Products and Services," http://www.genomichealth.com/products/default.aspx.

Genomic Health, 2004, "Oncotype DX Studies," http://www.genomichealth.com/oncotype/studies/default.aspx.

Goffeau et al., 1996, "Life with 6000 genes," Science 274:546-567.

Honigman et al., 2001, "Using Computerized Data to Identify Adverse Drug Events in Outpatients," Journal of the American Medical Informatics Association 8:255-266.

Hughes et al., 2000, "Functional Discovery via a Compendium of Expression Profiles," Cell 102:109-126.

IBM, "H. Lee Moffitt Cancer Center & Research Institute and IBM collaborate on new disease management system," Apr. 25, 2004.

International Human Genome Consortium, 2001, "Initial sequencing and analysis of the human genome," Nature 409:860-921.

Irby et al., 2002, "Increased Src Activity Disrupts Cadherin/Catenin-mediated Homotypic Adhesion in Human Colon Cancer and Transfored Rodent Cells," Cancer Research 62:2669-2674.

Johnston et al., 2000, "Outcomes of the Kaiser Permanente Tele-Home Health Research Project," Arch. Fam. Med. 9:40-45.

Kim et al., 2002, "Personal Health Records: Evaluation of Functionality and Utility," Journal of the American Medical Informatics Association 9:171-180.

Kruglyak et al., 2001, "Variation is the spice of life," Nature Genetics 27:234-236.

Kuperman et al., 1999, "Improving Response to Critical Laboratory Results with Automation: Results of a Randomized Controlled Trial," Journal of the American Medical Informatics Association 6:512-522.

Lander et al., 1989, "Mapping Mendelian factors underlying quantitative traits using RFLP linkage maps," Genetics 121:185-199.

Lander et al., 1994, "Genetic dissection of complex traits," Science 265:2037-2048.

Lander, 1996, "The new genomics: Global views of biology," Science 274:536-539.

Levsky et al., 2002, "Single-Cell gene expression profiling," Science 297:836-840.

Liotta et al., 2003, "Cancer's deadly signature," Nature Genetics 33:10-11.

Lockhart et al., 1996, "Expression monitoring by hybridization to high-density oligonucleotide arrays," Nature Biotechnology 14:1675-1680.

Lynch et al., 1988, *Genetics and Analysis of Quantitative Traits*, Sinauer Associates, Inc. Sunderland, MA, pp. 491-533.

Manning, 2004, "Moffitt Cancer Center to spend millions integrating new IBM system," Tampa Bay Business Journal.

Moore et al., 2002, "The Promise of Computerized Patient Record Systems for Office Practice," Seminars in Medical Practice 5:13-29.

Myeloma Focus, MMRF Winter 2001 Newsletter, vol. II, Issue III.

Olson et al., 1999, "Tutorial in biostatistics genetic mapping of complex traits," Statistics in Medicine 18:2961-2981.

Petrick et al., 2002, "Breast Cancer Detection: Evaluation of a Mass-Detection Algorithm for Computer-aided Diagnosis—Experience in 263 Patients," Radiology 224:217-224.

Report of the Leukemia, Lymphoma and Myeloma Progress Review Group, May 2001, National Cancer Institute.

Schena et al., 1995, "Quantitative monitoring of gene expression patterns with a complementary DNA microarray," Science 270:467-470.

Schena et al., 1996, "Parallel human genome analysis; microarray-based expression of 1000 genes," Proc. Natl. Acad. Sci. USA 93:10614-10619.

Shalon et al., 1996, "A DNA microarray system for analyzing complex DNA samples using two-color fluorescent probe hybridization," Genome Research 6:639-645.

Sidransky, David, "Emerging Molecular Marks of Cancer," Nature Reviews: Cancer, Mar. 2002, vol. 2.

Starmer et al., 2000, "Experience Using a Programmable Rules Engine to Implement a Complex Medical Protocol During Order Entry," Proc. AMIA Symp. 2000:829-32.

Tamayo et al., 1999, "Interpreting patterns of gene expression with self-organizing maps: Methods and application to hematopoietic differentiation," Proc. Natl. Acad. Sci. USA 96:2907-2912.

Tang et al., 1999, "Use of Computer-based Records, Completeness of Documentation, and Appropriateness of Documented Clinical Decisions," Journal of the American Medical Informatics Association 6:245-251.

Terwilliger et al., 1992, "A haplotype-based 'haplotype relative risk' approach to detecting allelic associations," Hum. Hered. 42:337-346.

Tsui et al., 2003, "Technical Description of RODS: A Real-time Public Health Surveillance System," Journal of the American Medical Informatics Association 10:399-408.

van't Veer et al, 2002, "Gene expression profiling predicts clinical outcome of breast cancer," Nature 415:530-536.

Yeatman, "The Future of Clinical Cancer Management: One Tumor, One Chip," The American Surgeon 69, pp. 41-44, Jan. 2003.

Yeoh et al., 2002, "Classification, subtype discovery, and prediction of outcome in pediatric acute lymphoblastic leukemia by gene expression profiling," Cancer Cell 1:133-143.

News Press article, Apr. 2004, Fort Myers News-Press, "Project takes aim at cancer," http://www.news-press.net/np/scripts/print.php, 2 pages.

Cathy Clark, May 2003, "Total Patient Care Extends to Community and Beyond," H. Lee Moffitt Cancer Center & Research Institute, Today's Tomorrows 11:15-17.

News to Note Column, Aug. 2003, "Cancer Center Hosts Third Annual Affiliate Conference," H. Lee Moffitt Cancer Center & Research Institute, Today's Tomorrows 11, Issue 2, p. 20.

H. Lee Moffitt Cancer Center & Research Institute, Feb. 2004, "National Functional Genomics Center," 8 pages.

H. Lee Moffitt Cancer Center & Research Institute, Mar. 2004, "The end of cancer in Florida begins with you," 4 pages.

PCT International Search Report dated Feb. 24, 2005, in International Application No. PCT/US2004/015133, filed May 14, 2004.

PCT International Preliminary Report on Patentability dated Nov. 14, 2006, in International Application No. PCT/US2004/015133, filed May 14, 2004.

Akagi, H, et al., "Microsatellite DNA markers for rice chromosomes," Theor Appl Genet, 93:1071-1077, 1996.

Amoreira, C, et al., "An improved version of the DNA methylation database (MethDB)," Nucleic Acids Res, 31(1):75-77, 2003.

Barbosa, J, et al., "The genetic heterogeneity of diabetes: histocompatibility antigens (HLA) in families with maturity-onset type diabetes of the young (MODY) and juvenile, insulin-dependent diabetes (JID)," Diabete Metab, 2(3):160, 1976.

Blanchard, A, "Synthetic DNA arrays," Genet Eng, 20:111-123, 1998.

Blanchard, AP, et al., "High-density oligonucleotide arrays," Biosensors & Bioelectronics, 11(6/7):687-690, 1996.

Bligh, HFJ, et al., "A microsatellite sequence closely linked to the *Waxy* gene of *Oryza sativa*," Euphytica, 86:83-85, 1995.

Chirgwin, JM, et al., "Isolation of biologically active ribonucleic acid from sources enriched in ribonuclease," Biochemistry, 18(24):5294-5299, 1979.

Egholm, M, et al., "PNA hybridizes to complementary oligonucleotides obeying the Watson-Crick hydrogen-bonding rules," Nature, 365(6446):566-568, 1993.

Froehler, BC, et al., Synthesis of DNA via deoxynucleoside H-phosphonate intermediates, Nucleic Acids Res, 14(13):5399-5407, 1986.

Fullerton, SM, et al, "Apolipoprotein E variation at the sequence haplotype level: implications for the origin and maintenance of a major human polymorphism," Am. J. Hum. Genet, 67:881-900, 2000.

Helentjaris, T, et al, "Restriction fragment polymorphisms as probes for plant diversity and their development as tools for applied plant breeding," Plant Molecular Biology, 5:109-118, 1985.

Helm, D, et al., "Classification and identification of bacteria by Fourier-transform infrared spectroscopy," J Gen Microbiol, 137(1):69-79, 1991.

Hofmann, WK, "Relation between resistance of Philadelphia-chromosome-positive acute lymphoblastic leukaemia to the tyrosine kinase inhibitor STI571 and gene-expression profiles: a gene-expression study," Lancet, 359(9305):481-486, 2002.

Hu, J, and Quiros, CF, "Identification of broccoli and cauliflower cultivars with RAPD markers," Plant Cell Reports, 10:505-511, 1991.

James, OFW, and Day, CP, "Non-alcoholic steatohepatitis (NASH): a disease of emerging identity and importance," J Hepatol, 29(3):495-501, 1998.

Malek, RL, et al., "Identification of Src transformation fingerprint in human colon cancer," Oncogene, 21(47):7256-7265, 2002.

Maskos, U, and Southern, EM, "Oligonucleotide hybridizations on glass supports: a novel linker for oligonucleotide synthesis and hybridization properties of oligonucleotides synthesised in situ," Nucleic Acids Res, 20(7):1679-1684, 1992.

McBride, LJ, and Caruthers, MH, "An investigation of several deoxynucleoside phosphoramidites useful for synthesizing deoxyoligonucleotides," Tetrahedron Letters, 24(3):245-248, 1983.

Naumann, D, et al., "Microbiological characterizations by FT-IR spectroscopy," Nature,1351(6321):81-82, 1991.

Naumann, D, et al., The characterization of microorganisms by Fourier-transform infrared spectroscopy (FT-IR) In: Nelson, WH, editor, Modern techniques for rapid microbiological analysis. New York, NY, VCH Publishers; pp. 43-96, 1991.

Nguyen, C, et al., "Differential gene expression in the murine thymus assayed by quantitative hybridization of arrayed cDNA clones," Genomics, 29(1):207-216, 1995.

Oestreicher, JL, "Molecular classification of psoriasis disease-associated genes through pharmacogenomic expression profiling," Pharmacogenomics J, 1(4):272-287, 2001.

Paterson, AH, "The DNA revolution," In: Paterson, AH, editor, Genome mapping in plants. Academic Press/R.G. Landis Company, Austin, TX; pp. 7-21, 1996.

Patil, N, et al., Blocks of limited haplotype diversity revealed by high-resolution scanning of human chromosome 21, Science, 294(5547):1719-1723, 2001.

Pease, AC, et al., Light-generated oligonucleotide arrays for rapid DNA sequence analysis, Proc Natl Acad Sci USA, 91(11):5022-5026, 1994.

Prashar, Y, and Weissman, SM, "Analysis of differential gene expression by display of 3'end restriction fragments of cDNAs," Proc Natl Acad Sci USA, 93(2):659-663, 1996.

Ramaswamy, S, et al., "A molecular signature of metastasis in primary solid tumors," Nat Genet, 33(1):49-54, 2003.

Reeders, ST, et al., "A study of genetic linkage heterogeneity in adult polycystic kidney disease," Hum Genet, 76(4):348-351, 1987.

Sagliocco, F, et al., "Identification of proteins of the yeast protein map using genetically manipulated strains and peptide-mass fingerprinting," Yeast, 12(15):1519-1533, 1996.

Shevchenko, A, et al., "Linking genome and proteome by mass spectrometry: large-scale identification of yeast proteins from two dimensional gels," Proc Natl Acad Sci USA, 93(25):14440-14445, 1996.

St. George-Hyslop, PH, et al., "Genetic linkage studies suggest that Alzheimer's disease is not a single homogeneous disorder" Nature, 347(6289):194-197, 1990.

Struss, D, and Plieske, J, "The use of microsatellite markers for detection of genetic diversity in barley populations," Theor Appl Genet, 97:308-315, 1998.

Velculescu, VE, et al., "Serial analysis of gene expression," Science, 270(5235):484-487, 1995.

Welsh, J, and McClelland, M, "Fingerprinting genomes using PCR with arbitrary primers," Nucleic Acids Research, Nucleic Acids Res, 18(24);7213-7218, 1990.

Wu, KS, and Tanksley, SD, "Abundance, polymorphism and genetic mapping of microsatellites in rice," Mol Gen Genet, 241(1-2):225-235, 1993.

Younossi, ZM, et al., "Nonalcoholic fatty liver disease: an agenda for clinical research," Hepatology, 35(4):746-752, 2002.

* cited by examiner

| Clinical characterization | 52-x |
| --- | --- |
| ICD-9 code for clinical characterization | 302-1 |
| Date clinical characterization was made | 304-1 |
| ⋮ | |

Fig. 3

| Demographic characterization | 60-x |
| --- | --- |
| Gender | 402-x |
| Marital status | 404-x |
| Ethnicity | 406-x |
| Language | 408-x |
| Eye color | 410-x |
| Hair color | 412-x |
| Height | 414-x |
| Weight | 416-x |
| Social security number | 418-x |
| Name | 420-x |
| Date of birth / age | 422-x |
| Education status | 424-x |
| Primary physician | 426-x |
| Referring physician | 428-x |
| Referral source | 430-x |
| Patient disabilities | 432-x |
| Indication as to whether patient is a smoker | 434-x |
| Indication as to whether patient consumes alcohol | 436-x |
| Residential address of patient | 438-x |
| Patient telephone address | 440-x |
| Insurance carrier for a patient insurance policy | 442-x |
| Member indentifier number for insurance policy | 444-x |
| ⋮ | |

Fig. 4

| | |
|---|---|
| Molecular profile of subject based on biological specimen from subject 1 | 610-1 |
| Identity of cellular constituent 1 | 802-1 |
| Abundance level of cellular constituent 1 at time point 1 | 804-1-1 |
| Abundance level of cellular constituent 1 at time point 2 | 804-1-2 |
| ⋮ | |
| Abundance level of cellular constituent 1 at time point N | 804-1-N |
| Identity of cellular constituent 2 | 802-2 |
| Abundance level of cellular constituent 2 at time point 1 | 804-2-1 |
| Abundance level of cellular constituent 2 at time point 2 | 804-2-2 |
| ⋮ | |
| Abundance level of cellular constituent 2 at time point N | 804-2-N |
| ⋮ | |
| Identity of cellular constituent Y | 802-Y |
| Abundance level of cellular constituent Y at time point 1 | 804-Y-1 |
| Abundance level of cellular constituent Y at time point 2 | 804-Y-2 |
| ⋮ | |
| Abundance level of cellular constituent Y at time point N | 804-Y-N |

Fig. 8

FRONT END

CROSS-REFERENCE

This application is a divisional of U.S. patent application Ser. No. 10/846,977, entitled "Computer Systems and Methods for Providing Health Care," filed on May 14, 2004, the entire disclosure of which is incorporated herein in its entirety by reference.

FIELD OF THE INVENTION

The field of this invention relates to computer systems and methods for identifying and optimizing treatment regimens using molecular profiling and clinical characterization.

BACKGROUND

Diseases such as cancer, heart disease, autoimmune disease, neurodegenerative disorders and infectious disease are leading causes of death in the United States. For example, the American Cancer Society projects 1,334,100 new cases of cancer occurred in 2003 in the U.S. with about 556,500 deaths. The cost of such diseases also has a major economic impact on the United States of America. The National Institute of Health projects that cancer cost the U.S. $171.6 billion in 2002. Despite the enormous costs involved, treatment of diseases such as cancer is typically developed through consensus-based medicine using little or no data specific to individual patients. The use of such methods to care for patients having such diseases leads to inefficient and often ineffective health care.

Small changes in treatment of such diseases cannot only have a major impact on the health and well-being of society, it also has a monetary value. For example, in 2002, the cost of cancer for Florida alone was estimated to be $12.3 billion. See, for example, "2003 Cancer Facts and Figures," American Cancer Society, 2004. This includes direct medical costs, cost of lost productivity due to illness, and cost of lost productivity due to premature death. Decreasing the cost of cancer in Florida by just two percent, or $246 million, would be significant in the overall economic impact.

In the case of cancer, physicians are currently unable to understand a patient's specific type of cancer beyond the visual microscopic analysis of cells. Cancer researchers have studied the molecular mechanisms behind these visual changes in behavior for years, but have not had the capabilities to understand these changes in individual patients.

A survey of the literature shows that there is a growing appreciation for the information that molecular profiling can provide. For example Yeoh, E-J. et al., 2002, Cancer Cell 1:133-143 used gene microarray technology to determine the molecular signatures for seven different subtypes of pediatric leukemia. For some leukemia subgroups, a subset of the identified genes could predict whether patients were at high risk of relapse. Hofmann et al., 2002, The Lancet, 359:481-486 used gene expression signatures from HuGeneFL to identify a correlation between gene expression profiles of bone marrow samples of Ph+ ALL patients, and resistance to the drug Imatinib. Armstrong et al., 2002, Nature Genetics 30:41-47, developed clustering algorithms using microarray data, and employed them to show that lymphoblastic leukemia, with mixed lineage translocations (MLL), has a prognosis and gene expression signature that is distinct from AML or ALL thereby showing that molecular signatures can serve as a basis for identification of unique diseases. Ramaswamy et al., 2003, Nature Genetics 33:49-54, used various microarray platforms to show that, across multiple tumor types, molecular signatures can be used to predict metastasis and poor clinical outcome. Oestreicher et al., 2001, Pharmacogenomics J. 1:272-87, used microarray technology to perform a genome-wide scan of multiple psoriasis patients and showed 159 genes associated with the disease. A longitudinal study of two different treatment regimens showed that, for a subset of the 159 genes, transcript levels changed significantly in those who responded and, in some cases, preceded clinical improvement.

Thus, while there is a growing body of molecular profiling information, such information is typically not used to treat individual patients. Rather, a consensus based approach in which established treatment regimens are followed is the norm. Accordingly, given the above background, what is needed in the art are systems and methods that will allow physicians and patients to harness the capabilities of molecular medicine and develop evidence-based therapies for patients.

Discussion or citation of a reference herein will not be construed as an admission that such reference is prior art to the present invention.

SUMMARY

The present invention provides systems and methods by which patient specific treatment regimens are identified for each patient that is enrolled in a health care program. The invention uses a novel approach in which molecular profiles are obtained from one or more biological specimens from the patient. The molecular profiles are combined with a classical clinical characterization that is made by the patient's physician to form a comprehensive characterization of the patient's medical status. The comprehensive characterization is used to select a treatment regimen for the patient.

In the present invention, classical treatment regimens for known diseases are refined using the outcome of clinical trials as well as the clinical outcome of patients enrolled in the health care program. Thus, as more patients are enrolled in a health care program and treated with treatment regimens that consider the longitudinal molecular profile of the patient (the molecular profile of the patient at periodic instances during the course of the patient's treatment), more data becomes available to refine and improve the treatment regimens.

Another aspect of the present invention comprises novel systems and methods for using molecular profiling data from patients of remote facilities, termed affiliate facilities. Affiliate facilities are typically small medical facilities found in local communities. Patients that are too sick or otherwise handicapped to travel to a centralized medical facility can receive the same quality of care at the affiliate facility that is available at the centralized medical facility. In accordance with the invention, patients visit the affiliate facility and a physician makes a clinical characterization of the patient. Further, a biological specimen is taken from the patient. In some instances, the biological specimen is both a blood sample and a tumor sample. The biological specimens are shipped to a central health care facility or other form of diagnostic facility where molecular profiling of the samples is performed. The results of the clinical characterization and the molecular characterization are then reduced to electronic form and used to search for one or more treatment regimens. From this search, candidate treatment regimens are communicated to the patient's physician at the affiliate medical facility where a selection of a particular treatment regimen is made.

Yet another aspect of the present invention provides a computer program product for use in conjunction with a computer system. The computer program product comprises a computer readable storage medium and a computer program mechanism embedded therein. The computer program mechanism comprises one or more data structures associated with each patient in a plurality of patients enrolled in a health care program. The one or more data structures associated with each respective patient in the plurality of patients collectively comprise (i) a patient identifier for the respective patient, (ii) a molecular profile from a biological specimen obtained from the respective patient, and (iii) a clinical characterization of the respective patient. The computer program mechanism further comprises a plurality of treatment regimens and a therapeutic determination module. The therapeutic determination module includes instructions for identifying a treatment regimen, from among the plurality of treatment regimens, for a patient in the plurality of patients.

An aspect of the present invention provides a computer program product for use in conjunction with a computer system. The computer program product comprises a computer readable storage medium and a computer program mechanism embedded therein. The computer program mechanism comprises one or more data structures. The one or more data structures are dimensioned and configured to store medical information for a plurality of patients. The computer program mechanism further comprises a data entry module. The data entry module includes instructions for inputting a patient identifier for a patient in the plurality of patients into a data structure in the one or more data structures. The data entry module further includes instructions for inputting a molecular profile from a biological specimen obtained from the patient into a data structure in the one or more data structures. The data entry module also includes instructions for inputting a clinical characterization of the patient into a data structure in the one or more data structures. The computer program mechanism further comprises a treatment regimen module having instructions for receiving a plurality of treatment regimens. The computer program mechanism further comprises a therapeutic determination module having instructions for identifying a treatment regimen, from among the plurality of treatment regimens, for a patient.

Still another aspect of the invention provides a computer comprising a central processing unit and a memory, coupled to the central processing unit. In this aspect of the invention, the memory stores instructions for accessing one or more data structures associated with each patient in a plurality of patients enrolled in a health care program. The one or more data structures associated with each respective patient in the plurality of patients collectively comprises (i) a patient identifier for the respective patient, (ii) a molecular profile from a biological specimen obtained from the respective patient, and (iii) a clinical characterization of the respective patient. The memory further stores instructions for accessing a plurality of treatment regimens and instructions for accessing a therapeutic determination module. The therapeutic determination module comprises instructions for identifying a treatment regimen, from among the plurality of treatment regimens, for a patient in the plurality of patients.

Another aspect of the invention provides a computer for providing health care in accordance with a health care program. The computer comprises a central processing unit and a memory, coupled to the central processing unit. The memory stores one or more data structures. The one or more data structures are dimensioned and configured to store medical information for a plurality of patients. The memory further stores a data entry module comprising (i) instructions for inputting a patient identifier for a patient into a data structure in the one or more data structures, and (ii) instructions for inputting a molecular profile from a biological specimen obtained from the patient into a data structure in the one or more data structures, and (iii) instructions for inputting a clinical characterization of the patient into a data structure in the one or more data structures. The memory further stores a treatment regimen module comprising instructions for receiving a plurality of treatment regimens. The memory further stores a therapeutic determination module comprising instructions for identifying a treatment regimen, from among the plurality of treatment regimens, for a patient.

The present invention also provides a method of providing health care in accordance with a health care program. In the method, a treatment regimen, from among a plurality of treatment regimens, is identified for a patient based upon a molecular profile associated with the patient and a clinical characterization associated with the patient. The patient is one of a plurality of patients enrolled in a health care program. For each respective patient in a plurality of patients enrolled in the health care program, medical information is stored in one or more data structures associated with the respective patient, the one or more data structures for each respective patient in the plurality of patients collectively comprising (i) a patient identifier, (ii) a molecular profile from a biological specimen obtained from the respective patient, and (iii) a clinical characterization of the respective patient.

Still another aspect of the invention provides a medical card defined by a base constructed from a substantially flat piece of plastic having a first face and second face, at least one of the faces comprising indicia placed thereon. The indicia comprise an identification of a patient uniquely associated with the medical card and a magnetic strip bearing electronic information. The electronic information comprises an identification of the patient, a diagnosis of the patient, and an identification of a doctor that made the diagnosis.

Another aspect of the invention comprises a method implemented by a computer system coupled to a wide-area network (WAN). The method comprises retrieving, over the WAN, one or more data structures for a patient in a plurality of patients enrolled in a health care program. The one or more data structures for the patient collectively comprise (i) a patient identifier, (ii) a molecular profile from a biological specimen, whereby the biological specimen was obtained from the patient at a first health care facility; and (iii) a clinical characterization of the patient. Next, one or a plurality of treatment regimens that are deemed suitable for the patient based upon the molecular profile and the clinical characterization are retrieved over the WAN.

Yet another embodiment of the present invention provides a method. In the method, a signed consent form is obtained from a patient at a first health care facility, thereby enrolling a patient in a health care program. A biological specimen is removed from the patient at the first health care facility and a clinical characterization of the patient is made at the first health care facility. Then, a molecular profile is created from the biological specimen at a location other than the first health care facility. Data relating to the patient is stored at one or more locations addressable by a wide-area network (WAN) that includes a node at the health care facility. The data that is stored includes an identification of the patient, the clinical characterization of the patient, and the molecular profile of the patient.

Still another aspect of the invention comprises a first computer and one or more second computers. The first computer is in electronic communication with each of one or more second computers over a wide area network (WAN). The first computer is associated with a first health care facility. The first computer comprises a first memory having instructions for retrieving, over the WAN, one or more data structures for a patient in a plurality of patients enrolled in a health care program. The one or more data structures for the patient collectively comprise (i) a patient identifier, (ii) a molecular profile from a biological specimen, wherein the biological specimen was obtained from the patient at the first health care facility; and (iii) a clinical characterization of the patient that was made at the first health care facility. The first memory further comprises instructions for retrieving, over the WAN, one or a plurality of treatment regimens that are deemed suitable for the patient based upon the molecular profile and the clinical characterization. The one or more second computers are at one or more locations other than the first health care facility. Further, the one or more second computers comprise one or more second memories that collectively comprise one or more data structures for each patient in a plurality of patients enrolled in the health care program. The one or more data structures for each respective patient in the plurality of patients collectively comprises (i) a patient identifier for the respective patient, (ii) a molecular profile from a biological specimen obtained from the respective patient, (iii) and a clinical characterization of the respective patient.

DESCRIPTION OF DRAWINGS

FIG. 3 illustrates a data structure for storing a clinical characterization of a patient in accordance with one embodiment of the present invention.

FIG. 4 illustrates a data structure for storing a demographic characterization of a patient in accordance with one embodiment of the present invention.

FIG. 8 illustrates a data structure for storing a molecular profile of a biological specimen obtained from a patient in accordance with an embodiment of the present invention.

Like reference numerals refer to corresponding parts throughout the several views of the drawings.

DETAILED DESCRIPTION

How patients will participate in and benefit from the methods of the present invention best illustrates the invention. Consider a patient enrolling in a system in accordance with the present invention system today and their treatment and again consider the same patient five years from now. Today, a newly diagnosed lung cancer patient entering the community-based healthcare system will receive treatment based upon consensus standards of practice that may or may not be the most current. Care delivery may be fragmented among the surgeon, radiologist and oncologist (if an oncologist is seen at all). Patient follow-up may be equally fragmented throughout the current community health delivery systems. The patient likely will not have the option of participating in a clinical trial.

Now consider a newly diagnosed lung cancer patient who elects to participate in a health care program in accordance with the present invention either at a centralized health care facility or at an affiliate health care facility that is closer to home. The patient signs a consent form that allows their data, including a biological specimen such as a tumor and/or blood sample, to be collected and studied to provide, in conjunction with the primary physician's clinical observations, a basis for care. The patient will have the opportunity to receive the best treatment protocols available to patients in the health care program and will have the option to enroll in a clinical trial. The patient will be monitored throughout their battle with their disease including diagnosis, prognosis and treatment. Their physicians, whether at the centralized health care facility or in the community, will be provided with real-time evidence-based treatment pathways based on the data that are collected.

Five years from now, patients will have the benefits of the discoveries and knowledge gained from the evidence gathered from previous patients enrolled in the health care program, e.g., treatment outcomes, understanding of molecular mechanisms derived from biological specimens, clinical trial data results, etc. The patient will receive the most current evidence-based treatments afforded to all patients in the health care program and will continue to have the option of participating in a clinical trial. A limited example of some of the diseases that can be treated using the methods of the present invention is disclosed in Section 5.10, below.

1. Overview of the Invention

Figure 1:
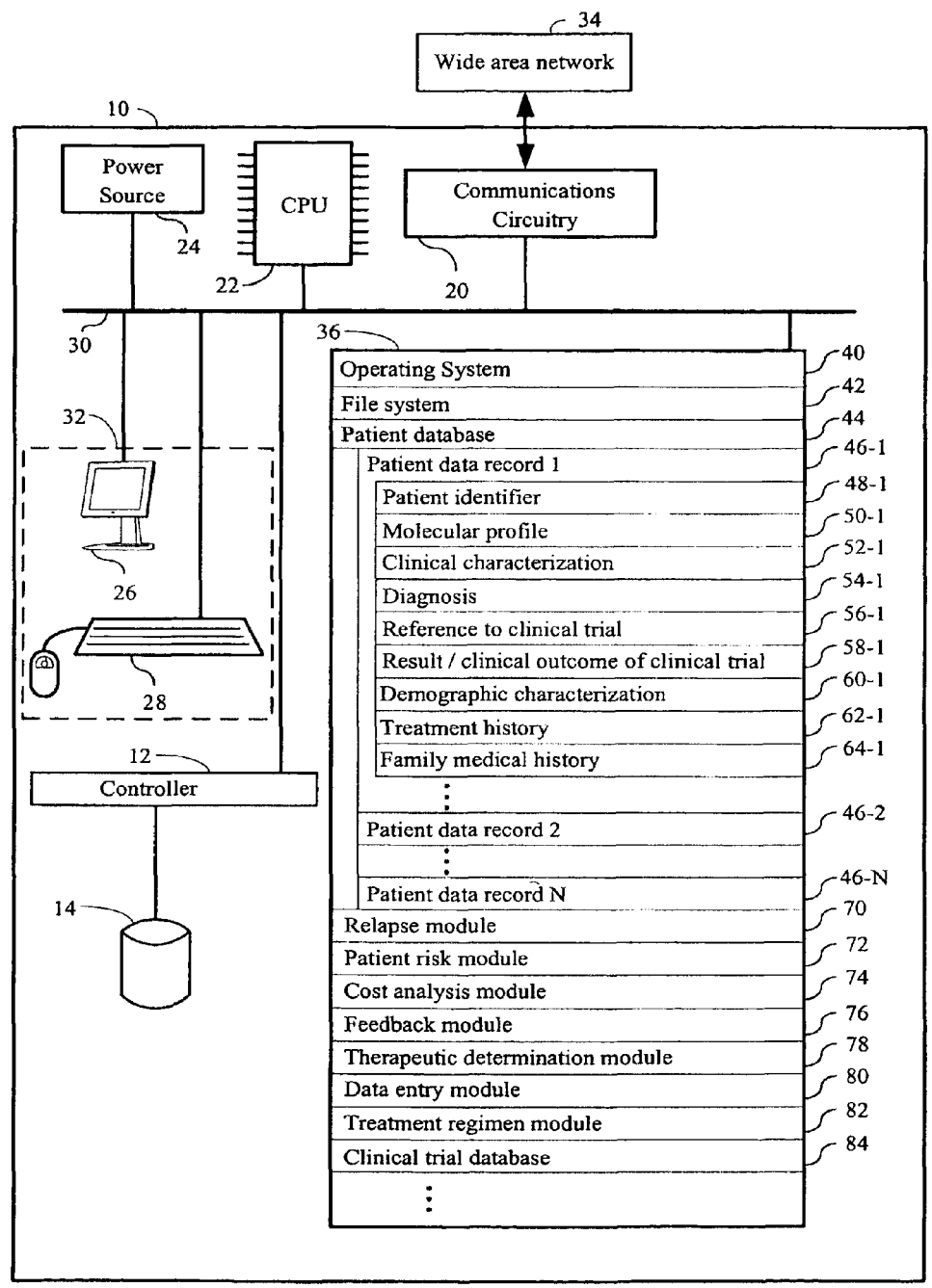
FIG. 1 illustrates a computer system for providing health care to patients enrolled in a health care program in accordance with one embodiment of the present invention.

FIG. 1 details an exemplary system that supports the functionality described above. The system is preferably a computer system 10 having:

a central processing unit 22;

a main non-volatile storage unit 14, for example a hard disk drive, for storing software and data, the storage unit 14 controlled by storage controller 12;

a system memory 36, preferably high speed random-access memory (RAM), for storing system control programs, data, and application programs, comprising programs and data loaded from non-volatile storage unit 14; system memory 36 may also include read-only memory (ROM);

a user interface 32, comprising one or more input devices (e.g., keyboard 28) and a display 26 or other output device;

a network interface card 20 for connecting to any wired or wireless communication network 34 (e.g., a wide area network such as the Internet);

an internal bus 30 for interconnecting the aforementioned elements of the system; and a power source 24 to power the aforementioned elements.

Operation of computer 10 is controlled primarily by operating system 40, which is executed by central processing unit 22. Operating system 40 can be stored in system memory 36. In a typical implementation, system memory 36 includes:

operating system 40;

file system 42 for controlling access to the various files and data structures used by the present invention;

one or more patient databases 44 for storing medical information associated with patients enrolled in a health care program;

a relapse module 70 for determining when a patient has relapsed;

a patient risk module 72 for identifying a patient registered in patient database 44 that is at risk for a disease;

a cost analysis module 74 for computing a cost for treating a patient;

a feedback module 76 for computing a cost for treating a patient;

a therapeutic determination module 78 for identifying a treatment regimen, from among a plurality of treatment regimens, for a patient registered in patient database 44;

a data entry module 80 for inputting a patient information into database 46;

treatment regimen module 82 for receiving a plurality of treatment regimens; and a clinical research repository 84 for storing clinical trial data.

As illustrated in FIG. 1, computer 10 comprises patient database 44. Database 44 can be any form of data storage system including, but not limited to, a flat file, a relational database (SQL), and an on-line analytical processing (OLAP) database (MDX and/or variants thereof). In some specific embodiments, database 44 is a hierarchical OLAP cube. In some specific embodiments, database 44 comprises a star schema that is not stored as a cube but has dimension tables that define hierarchy. Still further, in some embodiments, database 44 has hierarchy that is not explicitly broken out in the underlying database or database schema (e.g., dimension tables are not hierarchically arranged). In some embodiments, patient database 44 is a single database that includes patient data. In other embodiments, patient database 44 in fact comprises a plurality of databases that may or may not all be hosted by the same computer 10. In such embodiments, some component databases of "patient database 44" are stored on computer systems that are not illustrated by FIG. 1 but that are addressable by wide area network 34. Section 5.11 describes exemplary architectures for patient database 44.

It will be appreciated that many of the modules illustrated in FIG. 1 can be located on one or more remote computers. For example, some embodiments of the present application are web service-type implementations. In such embodiments, treatment regimen module 82 and other modules used by a physician to treat a patient can reside on a client computer that is in communication with computer 10 via network 34. In some embodiments, for example, treatment regimen module 82 and other modules used by a physician to treat a patient can be an interactive web page.

In some embodiments, the database 44 and modules (e.g. modules 70, 72, 74, 76, 78, 80, and 82) illustrated in FIG. 1 are on a single computer (computer 10) and in other embodiments the database 44 and modules are hosted by several computers (not shown). Any arrangement of database 44 and the modules illustrated in FIG. 1 on one or more computers is within the scope of the present invention so long as these components are addressable with respect to each other across network 34 or other electronic means. Thus, the present invention fully encompasses a broad array of computer systems.

2. Exemplary Patient Database

Now that an overview of the components of a system in accordance with the present invention has been described, a more detailed description of a patient database in accordance with one aspect of the invention follows. Patient database 44 includes a plurality of patient records 46. There is no limit on the number of patient records 46 that can be held in patient database 44. Database 44 can hold as few as one patient record 46. More typically, database 44 holds between 1 and 100 patient records, more than 100 patient records, more than a thousand patient records, more than ten thousand patient records, more than 100 thousand patient records, or between 1 patient record and one million patient records. Each patient record 46 preferably includes a patient identifier 48. As those skilled in the database arts will appreciate, a patient identifier 48 need not be explicitly enumerated in certain database systems. For instance, in some systems, a patient identifier 48 can simply be a patient record 46 identifier. However, in some embodiments, a patient identifier 48 can be a number that uniquely identifies a patient within a health care program.

An advantage of database 44 is that it has the capability of tracking molecular profile information 50 and clinical characterization information 52 for each patient registered in database 44. In some embodiments, a molecular profile 50 is the abundance levels of a plurality of cellular constituents in a biological specimen obtained from the patient. In some embodiments, such abundance levels are normalized using any of the techniques disclosed in Section 5.6. Representative biological specimens include, but are not limited to, a blood sample, a component of the patient's blood, and/or all or a portion of a tumor obtained from the patient. In some embodiments, a biological specimen is a tumor that is surgically removed from the patient, grossly dissected, and snap frozen in liquid nitrogen within twenty minutes of surgical resection.

In some embodiments, a molecular profile 50 comprises the processed microarray image data from the biological specimen obtained from the patient. In one example, molecular profile data 50 comprise cellular constituent abundance information for all or a portion of the cellular constituents represented in a microarray, optional background signal information, and optional associated annotation information describing the probe used for the respective cellular constituent. Cellular constituents include, but are not limited to RNA (e.g., mRNA) and protein.

In some embodiments, a molecular profile 50 represents the transcriptional state of cellular constituents in a biological specimen. See, for example, Section 5.8 below. However, in other embodiments, a molecular profile can track aspects of the biological state other than or in addition to transcriptional state. Such other aspects of the biological state include, but are not limited to, the translational state, the activity state of cellular constituents in a biological sample. See, for example, Section 5.9, below. In some embodiments, for example, molecular profile data 50 is, in fact, protein levels for various proteins in the biological specimen from the patient. Thus, in some embodiments, molecular profiles 50 comprise amounts or concentrations of the cellular constituent in biological specimens, cellular constituent activity levels in biological specimens, the state of cellular constituent modification (e.g., phosphorylation) in biological specimens, or other measurements.

In one embodiment, the amount of at least one cellular constituent that is tracked in a molecular profile 50 comprises abundances of at least one RNA species present in one or more cells in the biological specimen obtained from the patient. Such abundances can be measured by a method comprising contacting a gene transcript array with RNA derived from one or more cells of the biological specimen, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of the biological specimen, or with nucleic acid derived from the RNA, such that the gene transcript array comprises a positionally addressable surface with attached nucleic acids or nucleic acid mimics, where the nucleic acids or nucleic acid mimics are capable of hybridizing with the RNA species, or with nucleic acid derived from the RNA species.

In some embodiments, a molecular profile 50 can include abundance information or activity information about ten or more cellular constituents (e.g., genes or proteins), between ten and one thousand cellular constituents, between one thousand and twenty thousand cellular constituents, or more than twenty thousand cellular constituents.

In some embodiments, in addition to or rather than providing abundance information or activity information for cellular constituents, a molecular profile 50 tracks cellular constituent marker information. Such genetic marker information includes, but is not limited to, single nucleotide polymorphisms (SNPs), SNP haplotypes, microsatellite markers, restriction fragment length polymorphisms (RFLPs), short tandem repeats, sequence length polymorphisms, DNA methylation, random amplified polymorphic DNA (RAPD), amplified fragment length polymorphisms (AFLP), and "simple sequence repeats." For more information on molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., 7-21.

SNPs occur approximately once every 600 base pairs in the genome. See, for example, Kruglyak and Nickerson, 2001, Nature Genetics 27, 235. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, Am. J. Hum. Genet. 67, 881. Such haplotype structure is used in some embodiments of the present invention. Patil et al. found that a very dense set of SNPs is required to capture all the common haplotype information. See Patil et al., 2001, Science 294, 1719-1723. DNA methylation is described in Grunau et al., 2003, Nucleic Acids Res. 31, pp. 75-77.

RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, Plant Mol. Bio. 5:109-118, and U.S. Pat. No. 5,324,631).

The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511). AFLP technology refers to a process that is designed to generate large numbers of randomly distributed molecular markers (see, for example, European Patent Application No. 0534858 A1).

"Simple sequence repeats" or "SSRs" are di-, tri- or tetra-nucleotide tandem repeats within a genome. The repeat region can vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071-1077; Bligh et al., 1995, Euphytica 86:83-85; Struss et al., 1998, Theor. Appl. Genet. 97, 308-315; Wu et al., 1993, Mol. Gen. Genet. 241, 225-235; and U.S. Pat. No. 5,075,217). SSR are also known as satellites or microsatellites.

In addition to molecular profiles 50, patient records 46 include clinical characterizations 52. In some embodiments, a clinical characterization 52 comprises observations made by a patient's physician. In some instances, the observations made by a physician include a code from the International Classification of Diseases, $9^{th}$ Revision, prepared by the Department of Health and Human Services (ICD-9 codes), or an equivalent, and dates such observations were made. FIG. 3 illustrates a clinical characterization data structure in accordance with the present invention. The data structure includes an ICD-9 code (302) for each patient ailment and each corresponding date 304 such characterizations were made. Clinical characterization 52 complements information found within molecular profile 50. The clinical characterization 52 can include laboratory test results (e.g., cholesterol level, high density lipoprotein/low density lipoprotein ratios, triglyceride levels, etc.), statements made by the patient about their health, x-rays, biopsy results, and any other medical information typically relied upon by a doctor to make a diagnosis of the patient.

Patient records 46 further include diagnosis field 54. Diagnosis field 54 represents the diagnosis for the patient corresponding to the patient data record 46 based upon an analysis of the molecular profile 50 associated with the patient and the clinical characterization 52 associated with the patient.

Patients enrolled in health care programs in accordance with the present invention preferably have the opportunity to enroll in clinical trials that are designed to test, discover and/or optimize application of one or more drugs or other forms of treatment regimens. As such, patient record 46 can optionally include a reference 56 to a clinical trial to which the patient is enrolled. Furthermore, patient record 46 can store, reference, or otherwise include the results and/or clinical outcome of such a clinical trial in field 58. In some embodiments, information regarding the clinical trial itself is stored in commercial clinical trial products sold by companies such as InferMed, Ltd., London UK, (www.infermed.com), Phase Forward Inc., Waltham, Mass., (www.phaseforward.com), CB Technology, Philadelphia, Pa., (www.cbtech.com), DataTRAK Cleveland, Ohio, (www.datatraknet.com), Araccel, Stockholm, Sweden, (www.araccel.com), and TEAMworks, Hanover, Germany (www.teamworks.de).

Patient records 46 can optionally further include a demographic characterization 60 of respective patients. In some instances, relevant portions of the demographic characterization 60 can be used in conjunction with diagnosis 54 to select a treatment regimen for a patient. Referring to FIG. 4, in some embodiments, the demographic characterization for a respective patient comprises a gender 402 of the patient, a marital status 404 of the patient, an ethnicity 406 of the patient, a primary language 408 spoken by the patient, the color of the eyes 410 of the patient, the hair color 412 of the patient, the height 414 of the patient, the weight 416 of the patient, the social security number 418 of the patient, the name 420 of the patient, the date of birth 422 of the patient, the educational status 424 of the patient, an identity of the primary physician 426 for the patient, a name of a referring physician 428 for the patient, a referral source 430 for the patient, an indication 432 as to whether the patient is disabled and a description of the disability, an indication 434 as to whether the patient is a smoker, an indication 436 as to whether the patient consumes alcohol, a residential address 438 of the patient, and/or a telephone number 440 of the patient. In addition, the demographic characterization 60 can include a name of an insurance carrier 442 for an insurance policy held by the patient and/or a member identifier number 444 for an insurance policy held by the patient.

Patient data records 46 further includes a patient treatment history 62. Treatment history 62 indicates the treatment given to a patient and when such treatment was given. Treatment history 62 includes all prescriptions given to the patient and all medical procedures undergone on the patient. In some embodiments, the medical procedures include Current Procedural Terminology (CPT) codes developed by the American Medical Association for the procedures performed on the patient and a date such procedures were performed on the patient.

In some embodiments, a patient data record 46 includes a family medical history 64 in order to guide the selection of an appropriate treatment regimen for the patient. Family medical history 64 can include data such as whether or not a member of the patient's family has a disease, the molecular profile of biological samples taken from family members and the like.

In some embodiments directed to cancer, a patient data record 46 includes pathology data (e.g., world health organization (classification, tumor, nodes, metastases staging, images), radiographic images (e.g., raw, processed, cat scans, positron emission tomography), demographic data 60 (e.g., age, sex, etc.), laboratory data, Cerner electronic medical record data (hospital based data), molecular profile 50 (e.g. gene expression data), family history 64, risk factor data, access to a clinical reporting and data system, reference to vaccine production data/quality assurance, reference to a clinical data manager (e.g., OPTX), and reference to a cancer registry such as a research specimen banking database.

3. Exemplary Methods

Figure 2:
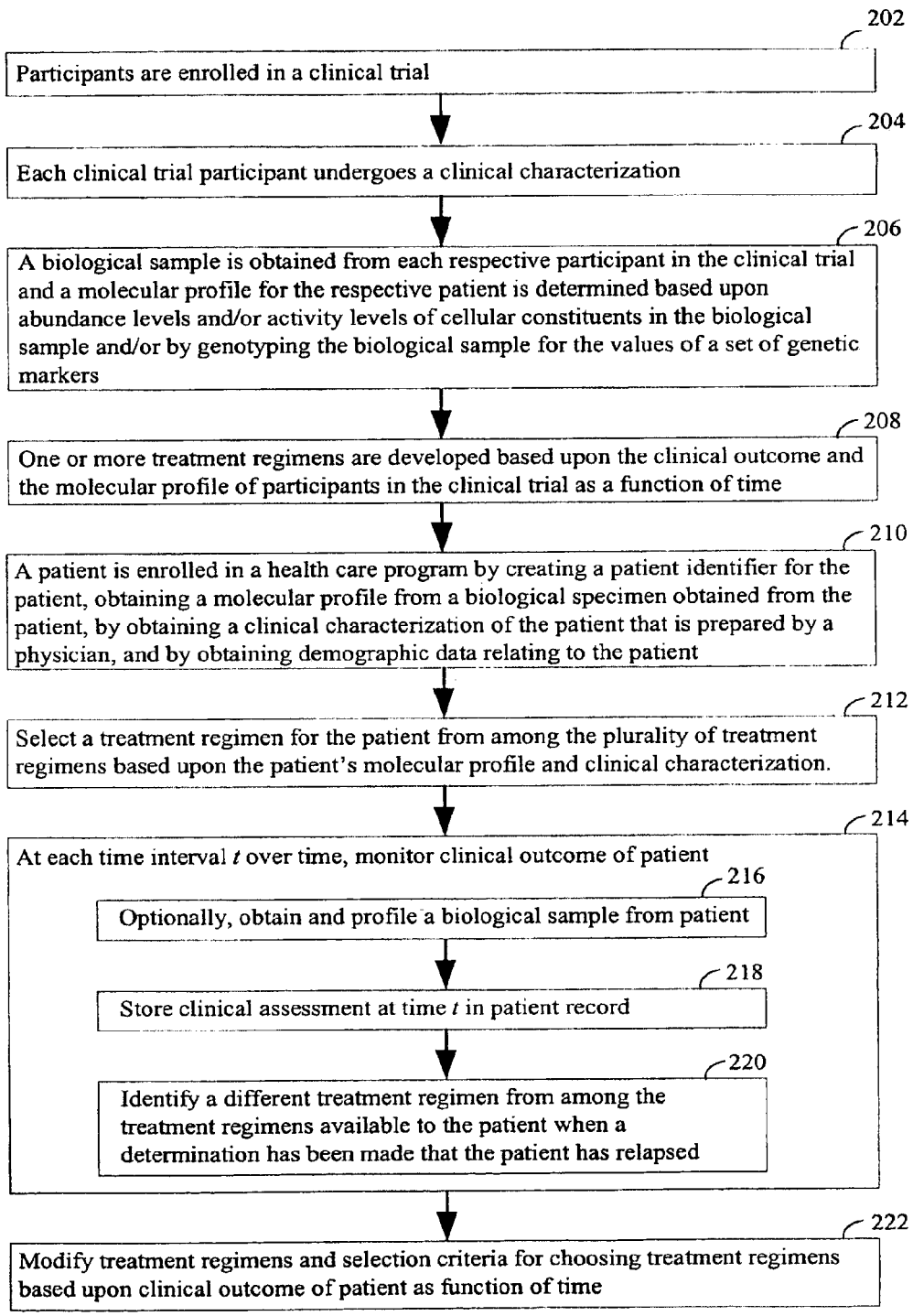
FIG. 2 illustrates a method for selecting a treatment regimen for a patient based upon a clinical characterization and a molecular profile of a specimen taken from the patient in accordance with an embodiment of the present invention.

Now that an overview of a system in accordance with one embodiment of the present invention has been described, various advantageous methods that can be used in accordance with the present invention will now be disclosed in this section in conjunction with FIGS. 2 and 8. The method disclosed in FIG. 2 can be divided into three parts. In the first part, steps 202-208, treatment regimens are optimized for a particular human disease using a clinical trial approach. In the second part, steps 210-220, a diagnosis is made and a treatment regimen is selected based upon a molecular profile from one or more biological specimens obtained from the patient in addition to a clinical characterization of the patient that is prepared by the patient's physician. In the third part, treatment regimens and selection criteria for choosing treatment regimens are modified based upon the clinical outcome of the patient in part two. Now that an overview of the method has been described, a more detailed description of the method will be presented.

Step 202. In step 202 a population is enrolled in a clinical trial. In some embodiments, 10 or more subjects are enrolled in a clinical trial. In some embodiments, between 10 and 100 subjects are enrolled in a clinical trial. In still other embodiments, between 100 and 500, between 500 and 1000, or more than 1000 subjects are enrolled in a clinical trial. In some embodiments, the clinical trial is a prevention trial, screening trial, quality-of-life trial, a treatment trial, or a diagnostic trial.

Prevention trials look for ways to reduce the risk of developing a particular disease or preventing it from coming back. These trials test the usefulness of certain medicines, vitamins, minerals or other supplements. The medicine or supplement that is chosen for a clinical trial is one that researchers believe may be able to lower cancer risk. Other prevention trials explore whether exercise, quitting smoking, eating more vegetables and fruit or other lifestyle choices help to prevent the disease.

Screening trials test or evaluate the best ways to detect the disease, especially in its early stages. In some cases, detecting the disease early can improve the results of treatment and increase the chances of survival. One example of a screening trial is the study of new medical imaging methods. Another example might be a new type of blood test that would detect clues that, for example, cancer can be present in a person's body. These trials usually involve people who may be at higher-than-average risk of developing the disease.

Quality-of-life trials (also called supportive care trials) study how to improve comfort levels and quality of life for people with a disease and disease survivors. For example, these trials may look at better ways to prevent or manage nausea, fatigue, depression, pain or other problems caused by the disease or its treatment.

Cancer treatment trials involve people with the disease. These trials usually compare new disease treatments with ones that already exist. The trials can be designed to answer issues such as (i) does the new treatment work better than the current best standard of care, (ii) will the new treatment reduce the chance that the disease will spread or come back, (iii) does the new treatment have fewer side effects than the current standard of treatment, and (iv) do most patients tolerate the side effects from the new treatment better. Treatments tested in clinical trials for cancer include, but are not limited to, (i) surgery—testing new techniques and timing of surgical procedures, (ii) chemotherapy—testing new drugs, drug combinations, different dosages and schedules of taking the drugs, (iii) hormone therapy—testing new ways to protect people with disease from the effects of various hormones on the disease, (iv) radiation therapy—testing new methods of delivering radiation or combining radiation with other disease therapies, (v) immunotherapy and vaccines—testing new treatments to stimulate and restore the body's own defenses, and developing vaccines against a particular type of disease, (vi) bone marrow and stem cell transplants—testing ways to protect the body while delivering more effective doses of chemotherapy or radiation, and (vii) anti-angiogenesis—studies drugs that kill cancers by blocking the growth of blood vessels that supply tumors.

Treatment trials are carried out in steps called "phases," the most prominent of which are phases I, II, and III. Phase I treatment trials are primarily concerned with assessing the safety of a drug. Phase I testing in humans is typically done in about 20 to 100 healthy volunteers. A phase I clinical study is designed to determine what happens to the drug in the patient. That is, how it is absorbed, metabolized, and excreted. In addition, by measuring the side effects of the drug at various dosage levels, a phase I study provides information on optimal drug dosage.

While a phase I treatment trial is directed to drug safety, a phase II treatment trial is directed to drug efficacy. A phase II treatment trial occurs after successful completion of a phase I treatment trial. A phase II treatment trial can last from several months to two years, and involve up to several hundred patients at numerous clinical sites throughout the world. Most phase II treatment trials are randomized trials. One group of patients receives the experimental drug while a control group receives a placebo or best standard treatment available. Often phase II treatment trials are "blinded" in the sense that neither the patients nor the researchers know who is getting the experimental drug. In this manner, the phase II treatment trial can provide a pharmaceutical company and a regulatory body, such as the United States Food and Drug Administration (FDA) of the United States or the European Commission (EC) of the European Union, comparative information about the efficacy of the new drug. If the phase II treatment trial is successful, a phase III treatment trial can be authorized. In some instances, marketing approval can be obtained based on a phase II trial, with a phase III trial following post-approval.

Typically, in a phase III treatment trial, the new drug is tested in several hundred to several thousand patients at hundreds of clinical sites throughout the world. This large-scale testing provides hospitals, pharmaceutical companies, and the regulatory agency with a more thorough understanding of the drug's effectiveness, benefits, and the range of possible adverse reactions. Most phase III treatment trials are randomized and blinded trials. Phase III treatment trials typically last several years.

Step 204. As is typically the case in a clinical trial, each clinical trial participant undergoes a clinical characterization. This clinical characterization is typically performed by a physician or other attending health care professional. One example of a clinical characterization is a physical examination, an electrocardiogram (EKG) a urinalysis, and/or a urine drug screen. Another example of a clinical characterization is a complete physical examination, blood tests, an electrocardiogram (ECG), chest x-ray, a bone marrow biopsy and/or skin tests. Still another example of a clinical characterization is muscle strength testing, vital lung capacity testing (breathing test) and/or questionnaires that ask specific questions about the participant's health, ability to function and quality of life. There are numerous other examples of clinical characterizations and all such characterizations are within the scope of the present invention. Further, each such clinical characterization is designed to obtain the information necessary to further the goals of the clinical trial.

Step 206. In some embodiments, a biological sample is obtained from trial participants in order to perform molecular profiling. This molecular profiling is used to obtain abundance levels and/or activity levels of a plurality of cellular constituents in the biological sample and/or to genotype the trial participants for a set of genetic markers. More details on molecular profiles that can be obtained in step 206 are found in Section 5.2.

Figure 9:
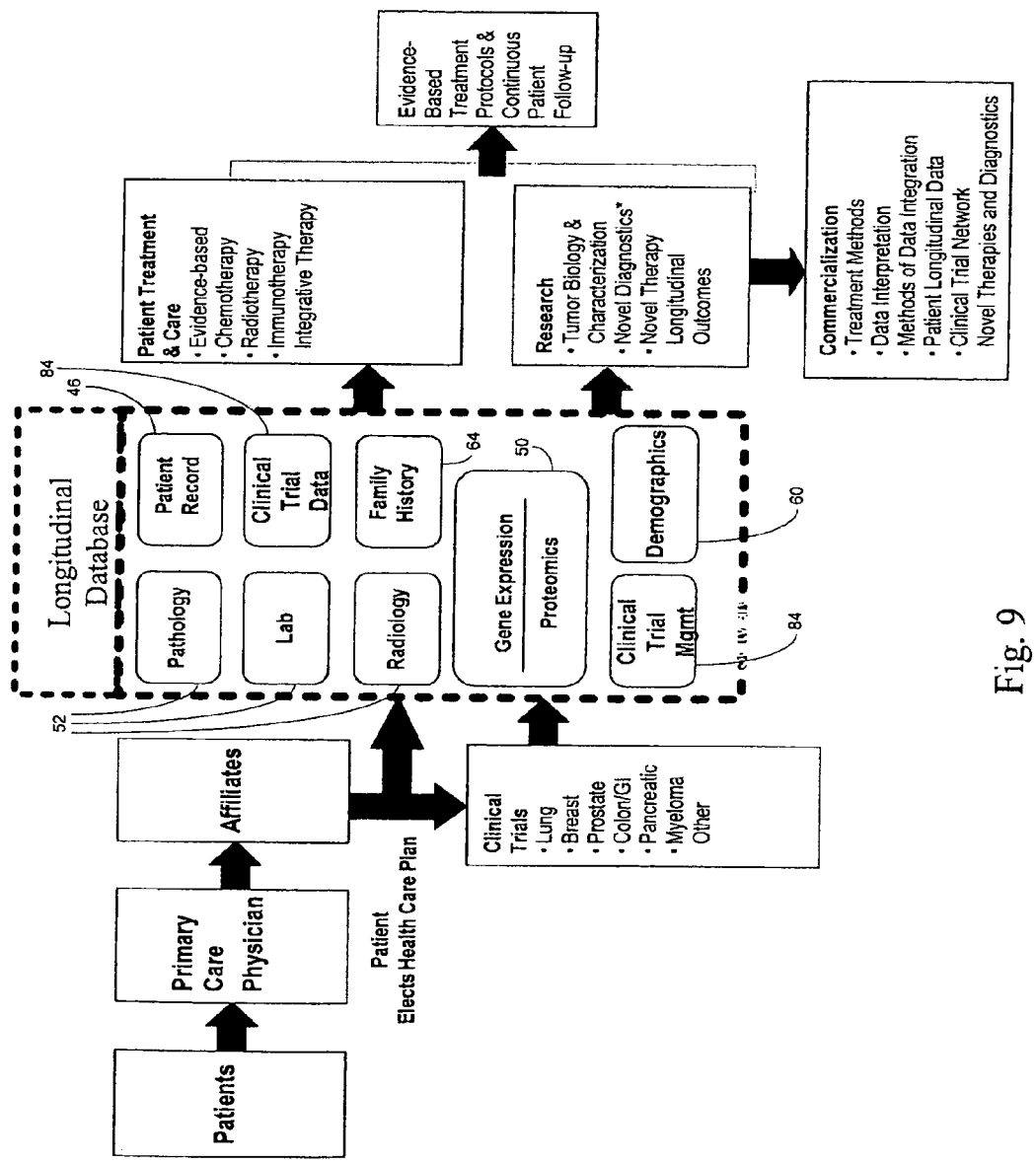
FIG. 9 illustrates how clinical trial data is used to develop treatment protocols, including "molecular signals" from biological specimens obtained from clinical trial participants, in accordance with one embodiment of the present invention.

Step 208. Once a clinical trial is completed, one or more treatment regimens are developed based upon the clinical outcome and the molecular profile of participants in the clinical trial, optionally as a function of time. In some embodiments, a clinical research repository 84 across all clinical research initiatives is maintained. Repository 84 serves as a single access, entry and retrieval point for clinical data including pathology, laboratory, patient record, and outcome data along with molecular profile data to create a unique data set. The synthesis of this clinical information is used to develop effective treatment regimens. FIG. 9 illustrates how clinical trial data are used to develop treatment protocols. Central to this approach is the ability to read the "molecular signals" from biological specimens, such as tumors, obtained from clinical trial participants.

In the approach described in FIG. 2, the molecular profiles of biological specimens from clinical trial participants will be classified based on the analysis of cellular constituents (e.g., gene transcripts, proteins) and/or characterization of genetic markers. In the case where the biological specimens are tumors, the molecular profile information is used to determine how tumors differ from normal tissues and how tumors differ from each other. Such molecular profiles can provide insights on how chemotherapies and radiation therapies affect the tumor, thereby leading to better understanding of the right treatment for the right patient at the right time.

By way of example, to conduct steps 202 through 208, the skilled artisan can use techniques similar to those in described in Malek et al., 2002, Oncogene 17, 7256-65. As described therein a classical rodent model of transformation was used to understand the transcriptional processes, and hence the molecular and cellular events a given cell undergoes when progressing from a normal to a transformed phenotype. The rationale behind this approach was the observation that Src activation is evident in 80% of human colon cancer, yet the myriad of cellular processes affected at the level of gene expression has yet to be fully documented. In the approach, a Src 'transformation fingerprint' within the gene expression profiles of Src-transformed rat 3Y1 fibroblasts was identified, demonstrating a progression in transformation characteristics. To evaluate the role of this gene set in human cancer development and progression, orthologous genes present on the Affymetrix Hu95A GeneChip (12 k named genes, Santa Clara, Calif.) and compared expression profiles between the Src-induced rodent cell line model of transformation and staged colon tumors where Src is known to be activated. A similar gene expression pattern between the cell line model and staged colon tumors for components of the cell cycle, cytoskeletal associated proteins, transcription factors and lysosomal proteins suggests the need for co-regulation of several cellular processes in the progression of cancer. Genes not previously implicated in tumorigenesis were detected, as well as a set of 14 novel, highly conserved genes with hereto-fore unknown function. These studies defined a set of transformation associated genes whose up-regulation has implications for understanding Src mediated transformation and strengthens the role of Src in the development and progression of human colon cancer. See, for example, Malek et al., 2002, Oncogene 17, 7256-65; and Irby et al., 2002, Cancer Research 62, 2669.

Another published report describes techniques that the skilled artisan can adapt to conduct steps 202-206 is described in Agrawal et al. See Agrawal et al., 2002, Journal of the National Cancer Institute 94, 513. Osteopontin was identified as a lead marker of colon cancer progression using pooled sample expression profiling. In the approach total RNA from human colon tumors (n=60) of multiple stages (adenomas, cancers with modified Collier stages B, C, and D, and liver metastases) were pooled within stages and compared with pooled normal mucosal specimens (n=10) by using oligonucleotide expression arrays. Genes that show consistent increases or decreases in their expression through tumor progression were identified. Northern blot analysis was used to validate the findings. All statistical tests were two-sided. The study identified more than 300 candidate tumor markers and more than 100 markers of tumor progression. Northern analysis of 11 candidate tumor markers confirmed the gene expression changes. Further, the gene for the secreted integrin-binding protein osteopontin was identified as a clinically useful marker of tumor progression. See, for example, Agrawal et al., 2002, Journal of the National Cancer Institute 94, 513.

Step 210. In step 210, a patient is enrolled in a health care program. In typical embodiments, a patient identifier is assigned to the patient and a molecular profile is derived from a molecular profile obtained from the patient. Further, a clinical characterization of the patient is made. In some embodiments, demographic data relating to patient is taken. More details on these types of information are described in Sections 5.1 and 5.2.

Step 212. In step 212, a treatment regimen for a patient is selected from among the plurality of treatment regimens available to treat a disease based upon the patient's molecular profile 50 and clinical characterization 52.

As an example, consider the case in which the patient has been diagnosed with colon cancer. At issue is the prognosis of the patient and what treatment regimen should be followed. One factor that can be used to address these issues is knowledge of the colon cancer stage. Following the work described in step 208 above, the level of osteopontin can be used to determine colon cancer stage (adenoma, AC stage C2 tumor, liver metastases). An appropriate therapy regimen can then be selected based upon the colon cancer stage. In other examples, identification of gene mutations in BRCA1 and BRCA2 in women is used as a basis for determining whether they have familial (genetic) related breast cancer, prostrate-specific antigen levels in men are used as a basis for determining whether the prostrate is undergoing changes that might indicate the presence of cancer, and the presence of HER2 is used as an indicator to suggest certain breast cancer patients should be given the cancer drug Herceptin.

Steps 214-220. Once a patient has been assigned a treatment regimen, the clinical outcome of the patient over time is periodically monitored. The frequency with which a patient is monitored will vary and is generally determined by the patient diagnosis. In some embodiments, the patient is monitored almost continuously. In other embodiments, the patient is monitored once a year, once a month, weekly, or daily.

Optionally, a biological sample is obtained from the patient during each monitoring instance (step 216). The biological sample can be, for example, a blood sample, a tissue sample, or a tumor sample. A molecular profile of each successive biological sample is preferably made. FIG. 8 illustrates a data structure 610 in which each of the successive molecular profiles can be stored. The data structure includes an identity of a plurality of a plurality of cellular constituents 802. In one embodiment, each cellular constituent is a human gene and each identifier 802 uniquely identifies a human gene. For each identified cellular constituents, there is an array 804 for storing the abundance level of the cellular constituent at various time points. For instance, record 804-1-1 stores the abundance level of the corresponding cellular constituent at a first time point, record 804-1-2 stores the abundance level of the corresponding cellular constituent at a second time point, and so forth.

During each monitoring instance, a clinical assessment of the patient, prepared by the patient's physician or other health care worker, is made and stored in the patient's record (step 218).

The clinical assessment (218) and updated molecular profile (216) can be used to identify a different treatment regimen from among the treatment regimens available to the patient when a determination has been made that the patient has relapsed.

Step 222. The longitudinal clinical assessments of patients in health care plans of the present invention that are obtained in step 214 above represents a resource for validating the efficacy of treatment regimens. In step 222, such longitudinal clinical assessments are used to modify treatment regimens and selection criteria for choosing such treatment regimens. For example, consider the case in which osteopontin levels are used as a basis for predicting colon cancer severity based on clinical trial research described in steps 202-206, above, and that, further, such levels are used as a basis for selecting the aggressiveness of the colon cancer treatment. In step 222, the historical longitudinal data from step 214 can be used to verify that osteopontin levels are an accurate indicator of colon cancer severity and that such levels provide a sound basis for deciding which treatment regimen to follow for a given patient.

4. Affiliate-Based Health Care

Longitudinal data derived using the methods disclosed in Section 5.3, including molecular signatures and outcome data should accelerate improvements in health care. Following a patient population having a disease or a population with significant rates of a disease, extracting tissue and blood samples, and applying genomics and proteomics technology should provide answers that lead to near-term reduction in mortality and ultimately to the prevention and cure of significant diseases. However, the use of molecular profiling in Section 5.3 for individual patients can lead to problems for patients that live far away from centralized health care facilities that have molecular profiling capabilities. This problem is particularly acute in instances where patients are too sick to travel to the health care facility or where frequent visits to the health care facility are required because of the protocol requirements of a clinical trial in which they are participating. Furthermore, health care facilities that do not have the computational resources and the molecular profiling resources cannot offer such medical care. This section discusses how such problems are addressed according to the present invention, by using affiliate health care centers, with reference to FIGS. 5-8.

Figure 7:
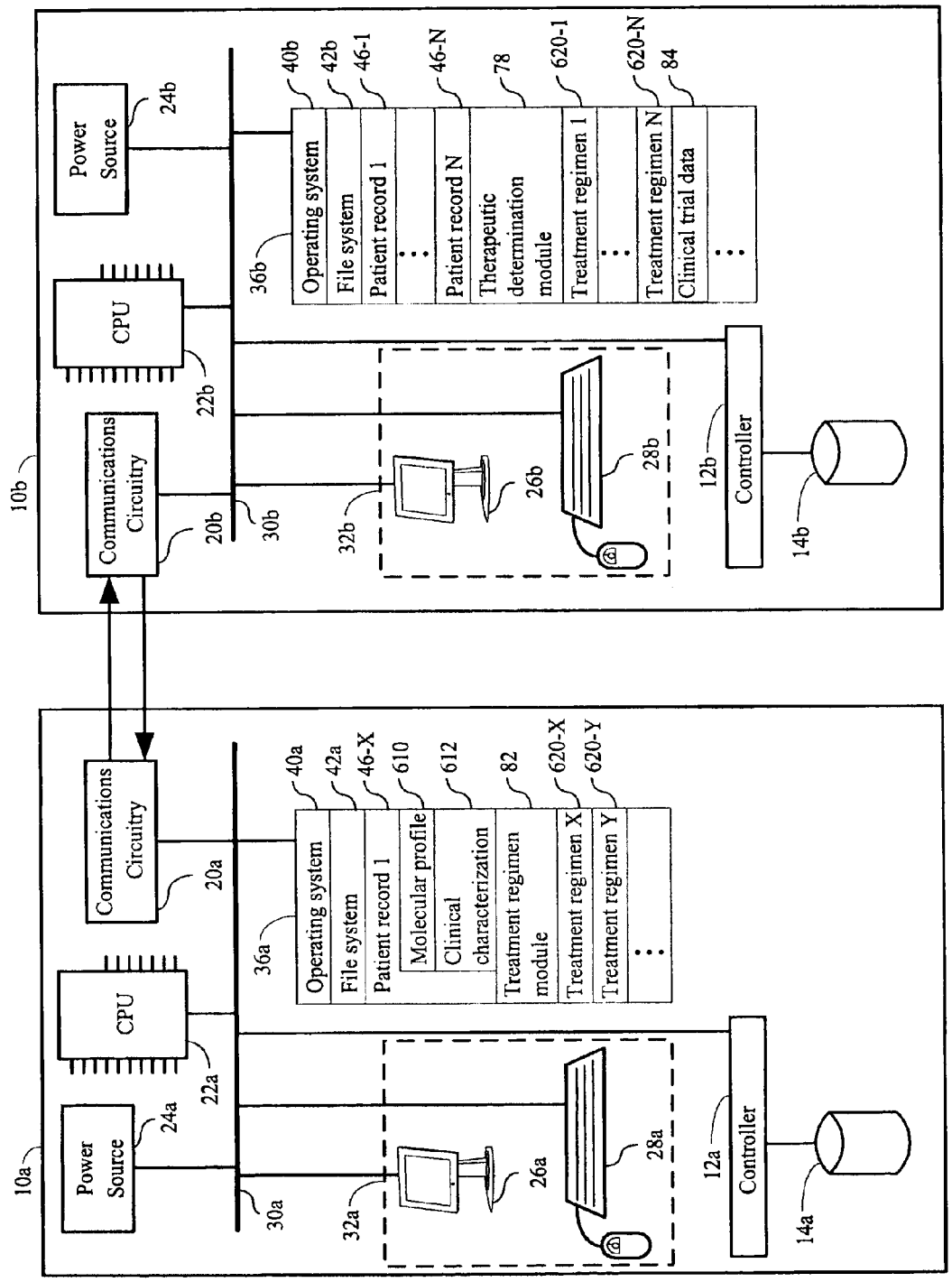
FIG. 7 illustrates a network topology for facilitating health care at an affiliate health care center using resources of a central health care facility in accordance with an embodiment of the present invention.

FIG. 7 illustrates a computer network that can be used to facilitate affiliated based implementation of the methods of the present invention. FIG. 7 describes a computer 10a that is at or accessible to an affiliate health care facility and a computer 10b that is at or accessible to a central health care facility. Computers 10a and 10b are in electronic communication with each other via a network such as a wide-area network (e.g., WAN).

Computer 10a includes a central processing unit 22a, a main non-volatile storage unit 14a, for example a hard disk drive, for storing software and data. Storage unit 14a is controlled by storage controller 12a. Computer 10a includes a system memory 36a, preferably high speed random-access memory (RAM), for storing system control programs, data, and application programs comprising programs and data loaded from non-volatile storage unit 14b. System memory 36a can also include read-only memory (ROM). Computer 10a further includes a user interface 32a, comprising one or more input devices (e.g., keyboard 28a) and a display 26a or other output device. Computer 10a further includes a network interface card 20a for connecting to any wired or wireless communication network (e.g., a wide area network such as the Internet) and an internal bus 30a for interconnecting the aforementioned elements of the system. Computer 10a further includes a power source 24a to power the aforementioned elements. Operation of computer 10a is controlled primarily by operating system 40a, which is executed by central processing unit 22a. Operating system 40a can be stored in system memory 36a. In a typical implementation, system memory 36a includes operating system 40a and file system 42a for controlling access to the various files and data structures used by the present invention.

Computer 10b includes a central processing unit 22b, a main non-volatile storage unit 14b, for example a hard disk drive, for storing software and data. Storage unit 14b is controlled by storage controller 12b. Computer 10b further includes a system memory 36b, preferably high speed random-access memory (RAM), for storing system control programs, data, and application programs comprising programs and data loaded from non-volatile storage unit 14b. System memory 36b can also include read-only memory (ROM). Computer 10b further includes a user interface 32b, comprising one or more input devices (e.g., keyboard 28b) and a display 26b or other output device. Computer 10b further includes a network interface card 20b for connecting to any wired or wireless communication network (e.g., a wide area network such as the Internet) and an internal bus 30b for interconnecting the aforementioned elements of the system. Computer 10b further includes a power source 24b to power the aforementioned elements. Operation of computer 10b is controlled primarily by operating system 40b, which is executed by central processing unit 22b. Operating system 40b can be stored in system memory 36b. In a typical implementation, system memory 36b includes operating system 40b and file system 42b for controlling access to the various files and data structures used by the present invention.

Computers 10a and 10b can exchange data using any form of network such as a direct link network (e.g., ethernet, token ring, etc.) or a packet switched network (e.g., Asynchronous Transfer Mode networks) using any suitable communication protocol such as the Internet Protocol. Further, computers 10a and 10b can be configured in any network using any communication protocol described in Peterson and Davie, Computer Networks A Systems Approach, Morgan Kaufmann Publishers, Inc., San Francisco, Calif.

The following exemplary steps describe the development of treatment regimens for a particular disease. However, one of skill in the art will appreciate that steps 502 thorough 506 can be repeated for as many different diseases as desired so that there exists treatment regimens for any disease of interest.

Step 502. Steps 502 through 506 of FIG. 5 bear similarity to steps 202 through 208 of FIG. 2. In some embodiments, steps 502 through 506 are performed at a central health care facility, an affiliate health care facility, or some other facility such as a research University or a hospital that is not affiliated with the affiliate health care facility of the central health care facility. In some embodiments, the results of steps 502 through 506 are taken from a publication, e.g. a peer reviewed journal article.

In step 502, subjects are examined using general research tools such as clinical trials in order to study diseases. Subjects in the clinical trial provide biological specimens (e.g., tumor sample, blood sample, etc.) for molecular profiling. The molecular profiling can be performed at the central health care facility or some other third party health care facility or some other facility that does not provide health care.

Step 504. In step 504, patients are tracked over time in order to develop longitudinal clinical trial results. In some embodiments, biological specimens are removed from trial participants each or at least some of the times they are examined during step 504 and successive molecular profiles of the biological specimens are made. The successive molecular profiles can be stored in a data structure such as 610 (FIG. 8). Data structure 610 is discussed in detail in Section 5.3.

Figure 5:
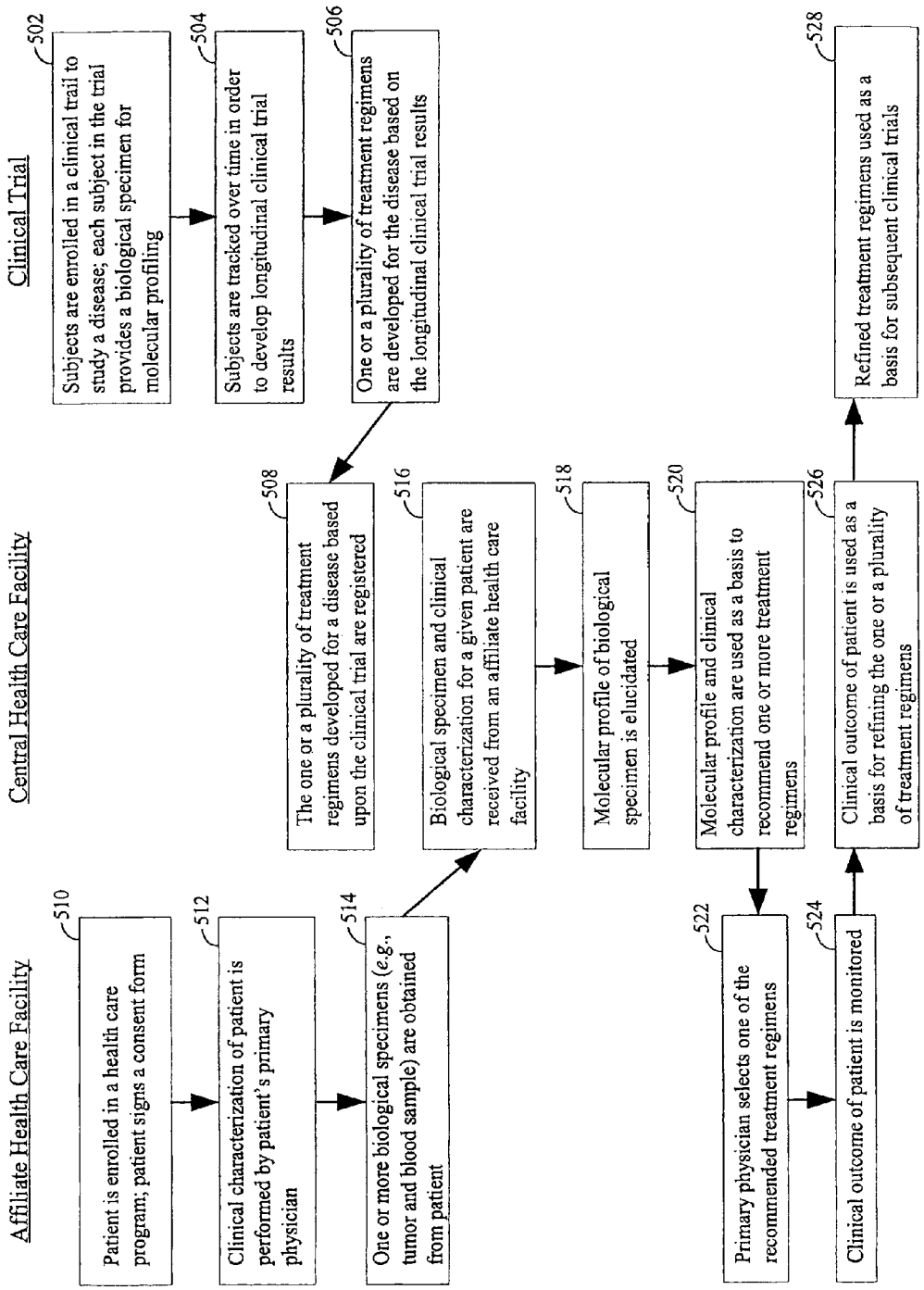
FIG. 5 illustrates a networked based topology for how a patient can receive health care at an affiliate health care facility in accordance with an embodiment of the present invention.
Figure 6:
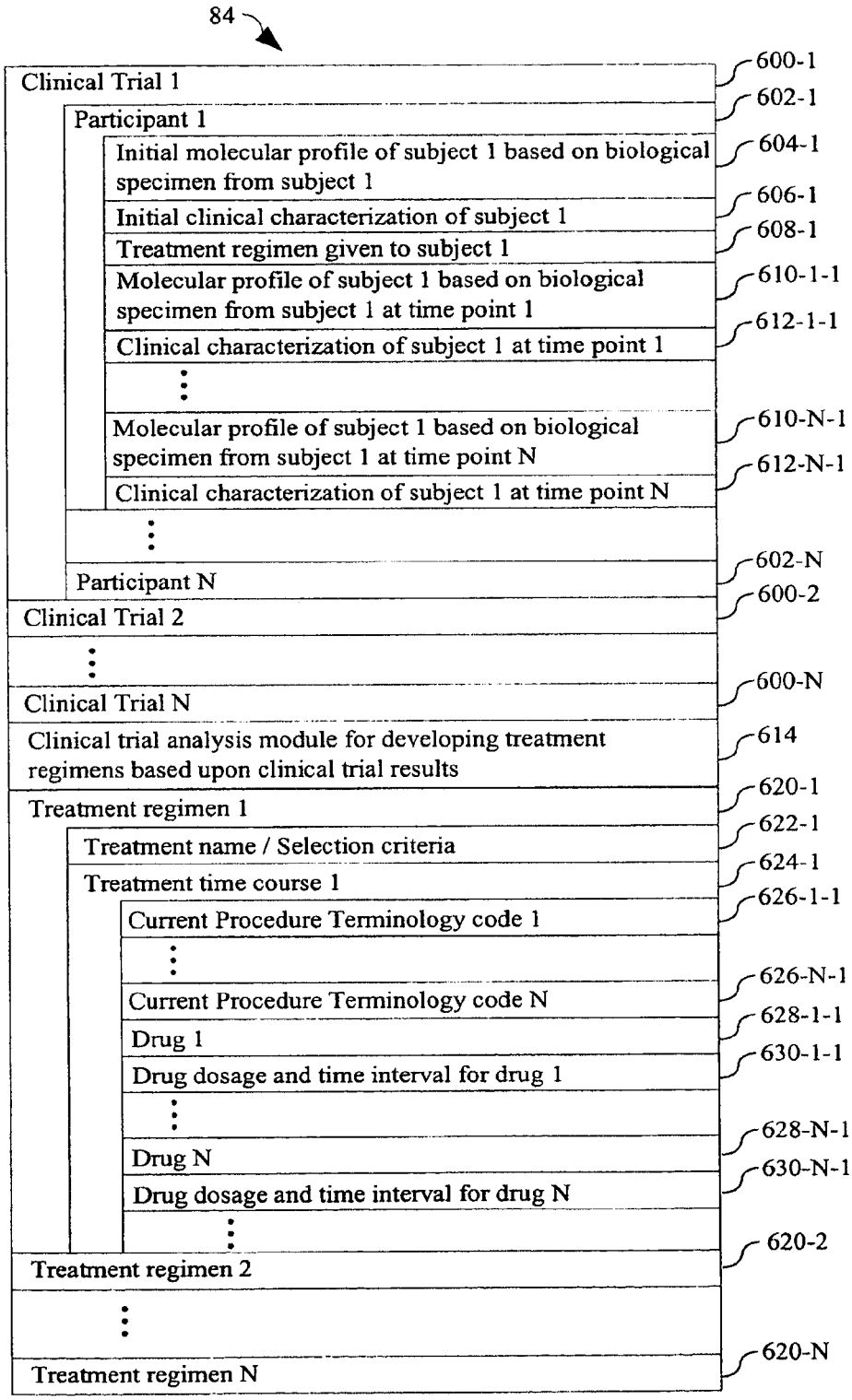
FIG. 6 illustrates a data structure for storing the results of a clinical trial and a plurality of treatment regimens in accordance with one embodiment of the present invention.

FIG. 6 illustrates a clinical research repository 84 for storing clinical trial results that are obtained in step 502-506 of FIG. 5. Clinical research repository 84 can be used to store the results of any number of clinical trials 600. For instance, the results of a first clinical trial are stored in data structure 600, the results of a second clinical trial are stored in data structure 600-2, the results of a third clinical trial are stores in data structure 600-3, and so forth. In some embodiments, clinical research repository 84 tracks only one clinical trial. In some embodiments, clinical research repository 84 tracks between two and twenty clinical trials. In some embodiments, clinical research repository 84 tracks between twenty and one hundred clinical trials. In still other embodiments, clinical research repository 84 tracks between one hundred and five hundred clinical trials. In still other embodiments, data structure tracks more than five hundred clinical trials.

In some embodiments, clinical research repository 84 is resident on a single computer. In other embodiments, clinical research repository 84 is partitioned across more than one computer. In some embodiments, clinical research repository 84 is partitioned across two or more computers, ten or more computers, or between five and one hundred computers. In some embodiments, each data structure 600 is partitioned across one or more computers at different locations.

Each clinical trial 600 includes a plurality of participants. In the data structure 84 illustrated in FIG. 6, each participant is assigned their own data structure 602. Each data structure 602 includes information about the corresponding subject such as an initial molecular profile base on a biological specimen that is obtained from the subject. In some embodiments, more than one type of biological specimen is obtained from the subject and another record is present (not shown) in the data structure 602 in order to store the molecular profile obtained from the biological specimen. In some embodiments, two or more different types of molecular profiles are created from a single biological specimen (e.g., gene expression profile, protein abundance assays, and genetic marker assays).

In addition to initial molecular profiles 604 for each trial participant, each respective data structure 602 includes an initial clinical characterization 606 of the subject. Such initial clinical characterizations can be the results of a physical examination, conventional assay test results, or any of the tests described in conjunction with the clinical characterizations of FIG. 1.

In some clinical trials, each trial participant is assigned a treatment regimen. Such treatment regimens may describe the administration and dosage of a drug, the administration of placebo, or some other form of treatment. The treatment for each trial participant 602 may be different. Therefore, each data structure 602 includes a field 608 to describe the treatment regimen assigned to the corresponding clinical trial participant.

At subsequent time intervals after the initial molecular profile and clinical characterization have been made, subsequent assessments can be made of the clinical trial participants in order to gauge the effectiveness of their treatment regimens 608. For example, at defined time points, additional biological specimens can be obtained from trial participants and used as the basis for additional molecular profiles. Such additional molecular profiles are stored in data structure 610. For example, a molecular profile obtained from a biological specimen from clinical participant 1 at a first time point after the initial time point is stored in data structure 610-1-1, a molecular profile obtained from a biological specimen from clinical participant 1 at a second time point after the initial time point is stored in data structure 610-2-1, and so forth. A representative data structure 610 has been described above in conjunction with FIG. 8. In addition to such molecular profiles, additional clinical characterizations can be made at each successive time point and stored in data structures 612. For example, a clinical characterization made of clinical participant 1 at a first time point after the initial time point is stored in data structure 612-1-1, a clinical characterization made of clinical participant 1 at a second time point after the initial time point is stored in data structure 612-2-1, and so forth.

Step 506. Returning to FIG. 5, in step 506, one or a plurality of treatment regimens are deduced for a disease based on the longitudinal results of the clinical trial. Referring to FIG. 6, in some embodiments clinical trial results are analyzed by module 614 (clinical trial analysis module for developing treatment regimens based upon clinical trial results). In some embodiments, the clinical trial results 600 are analyzed with pattern classification techniques such as clustering in order to identified cellular constituents that are up-regulated or down-regulated in the diseased state. In some embodiments, the clinical trial results 600 are analyzed to identify genetic markers that tend to be present (or absent) in the diseased states and absent (or present) in the normal state. Pattern classification techniques that can be used to make these association include but are not limited to (i) Bayesian analysis, (ii) nonparametric techniques such as Parzen windows, $k_n$-Nearest-neighbor estimation and fuzzy classification, (iii) linear discriminant functions such as Ho-Kashyap procedures and support vector machines, (iv) multilayer neural networks, (v) stochastic methods such as simulated annealing, deterministic simulated annealing, and genetic algorithms, (vi) nonmetric methods such as decision trees, classification and regression trees (CAR), (vii) algorithm-independent machine leaning techniques such as mixture-of-expert model, (viii) application of statistical tests such as chi-square tests, student's t-test or regression, (ix) supervised learning techniques such as linear regression and Kernel methods, boosting and additive trees, and (x) Markov networks. Such techniques are described in Duda, *Pattern Classification*, Second Edition, 2001, John Wiley & Sons, Inc., New York, N.Y.; Hastie, 2003, *The Elements of Statistical Learning, Data Mining, Inference, and Prediction*, Springer-Verlag, New York, N.Y.; Pearl, *Probabilistic Reasoning in Intelligent Systems*, Revised Second Printing, 1988, Morgan Kaufmann Publishers, Inc.; Spiegel and Stephens, *Statistics*, Third Edition, 1999, The McGraw-Hill Companies Inc, New York, N.Y.; Smith, *Statistical Reasoning*, 1991, Allyn and Bacon, Needham Heights, Mass.; and Bevington, *Data Reduction and Error Analysis for the Physical Sciences*, Second Edition, 1992, McGraw-Hill Companies, Inc., New York, N.Y. Such techniques are particularly useful in instances where the molecular profile data comprises cellular constituent abundance data (e.g., gene expression data, or data derived from proteomics). In instances where the molecular profile data include genetic marker data (e.g., genotypes) techniques such as the mapping and characterization of quantitative trait loci in outbred population and association techniques are useful. See, for example, Lynch and Walsh, *Genetics and Analysis of Quantitative Traits*, 1998, Sinauer Associates, Inc. Sunderland, Mass. (in particular, Chapter 16).

Referring to FIG. 6, there is shown a data structure 620 that stores the details of a treatment regimen for a disease under study. In preferred embodiments, each treatment regimen is stored in a different data structure 620. Each treatment regimen optionally has a name 622 and other information such as the clinical study or peer reviewed journal article that formed the basis of the treatment. Each treatment regimen 620 further includes selection criteria 622 that are used to select the treatment regimen 620 for use by a patient. There can be two types of selection criteria, clinical-based selection criteria and molecular profile-based selection criteria. Clinical-based selection criteria include determinations that the patient has a particular cancer (e.g., based on classical diagnostic assays) whereas expression-based selection criteria specify, for example, expression value ranges for particular cellular constituents, the presence, absence, or specific values of specific genetic markers, and the like.

Each treatment regimen 620 further includes a treatment time course 624. A treatment time course 624 specifies what treatment is to be given to a patient and when the treatment is to be given. For instance, in some embodiments of the present invention, treatment is divided into discrete longitudinal intervals and the treatment to be administered at each interval can be the same or different. At each time interval, the Current Procedure Terminology code 626 for one or more medical procedures to be performed on the patient is enumerated. Further, one or more drugs 628 and the respective drug dosages and time intervals 630 to be administered to the patient are enumerated. In some embodiments, the treatment regimen is not divided into time intervals. In some embodiments, the treatment regimen is divided into two or more time intervals. In such embodiments, the patient progresses from one time interval to the next when predetermined clinical criteria have been satisfied. For example, in some embodiments, each treatment regimen time interval corresponds to a different degree of severity in the patient's disease.

Step 508. Returning to FIG. 5, in step 508, the one or more treatment protocols developed in step 506 are communicated to the central health care facility where the treatment protocols are registered. For example, referring to FIG. 7, computer 10b can be associated with a central health care facility and, in step 508, the treatment regimens 620 developed in steps 502-506 can be stored in memory 36b of computer 10b.

Step 510. Steps 502 through 508 can be used in embodiments that do not involve or use affiliate health care facilities. In such embodiments, patients make use of the plurality of treatment regimens developed in preceding steps using methods such as those disclosed in Section 5.3 in conjunction with FIG. 2. However, in preferred embodiments, affiliate health care facilities are used to expand the patient population that can be considered for clinical trial participants, and to widen the network in which health care programs of the present invention can be implemented. For instance, as described above, usage of affiliate health care facilities allows patients that cannot readily travel to a centralized health care facility to fully participate in the health care program.

The affiliate-based aspects of the method begin when a patient is enrolled in a health care program at an affiliate health care facility. The patient signs a consent form that grants permission to have medical data obtained from the patient to be used to develop treatment protocols that can be applied to future patients. More specifically, the consent form grants health care workers permission to perform molecular profiling on biological specimens that is obtained from patients. As a result, a patient record 46 is created for the patient.

In some embodiments, the affiliate health care facility has 500 hospital beds or less. In some embodiments, the affiliate health care facility has greater than 500 hospital beds. In some embodiments, the affiliate health care facility has no hospital beds, between 1 and 500 hospital beds, between 500 and 1000 hospital beds, or more than 1000 hospital beds. In some embodiments, the central health care facility has 500 hospital beds or greater. In some embodiments, the central health care facility has between 500 and 1000 hospital beds, or more than 1000 hospital beds.

Step 512. In step 512, a clinical characterization of the patient is performed. In preferred embodiments, the clinical characterization is performed by the patient's primary physician at the affiliate health care facility. In some embodiments, the clinical characterization is performed by any health care official at the affiliate health care facility. The clinical characterization can include any form of medical test that is classically relied upon in the medical profession to diagnose a patient. Further, the forms of clinical characterization that can be obtained in step 512 can include any of the examples provided in preceding sections, such as the examples of the clinical characterizations 52 (FIG. 1). Referring to FIG. 7, the clinical characterization is stored in date structure 612 of the patient record 46 created for the patient in computer 10*a*.

Step 514. One or more biological specimens (e.g., tumor and blood sample) are also obtained from the patient while the affiliate is at the affiliate health care facility. In typical embodiments, the affiliate health care facility does not have the laboratory resources necessary to obtain a molecular profile from the biological specimens. Therefore, in typical embodiments, the biological specimens are transported to a central health care facility or other form of facility that is capable of performing molecular profiling. In typical embodiments the central health care facility is several miles away from the affiliate health care facility. For example, in some embodiments, the central health care facility is more than 10 miles away from the affiliate health care facility. In other embodiments, the health care facility is more than 100 miles away from the affiliate health care facility. In some embodiments, the molecular profile from the biological specimen is created at a location that is in a state other than the state where the affiliate health care facility is located. In some embodiments, the molecular profile from the biological specimen is created at a location that is in a country other than the country where the first health care facility is located.

In some embodiments of the present invention, the central health care facility, the affiliate health care facility, and the facility that performs the molecular profiling (profiling facility) are separated by a distance. Typically this distance is a number of miles. As such, in some embodiments, the central health care facility, the affiliate health care facility, and the profiling facility are each separated by one or more miles, between 1 and 100 miles, between 100 and 300 miles, or more than 300 miles. In some embodiments, at least two of the central health care facility, the affiliate health care facility, and the profiling facility are separated by one or more miles, between 1 and 100 miles, between 100 and 300 miles, or more than 300 miles. In some embodiments, the central health care facility, the affiliate health care facility, and the profiling facility are each in a different town, city, or county. In some embodiments, at least two of the central health care facility, the affiliate health care facility, and the profiling facility are in a different town, city, or county. In some embodiments, the central health care facility, the affiliate health care facility, and the profiling facility are each in a different state or country. In some embodiments, at least two of the central health care facility, the affiliate health care facility, and the profiling facility are in a different state or country.

The one or more molecular profiles for the patient are ultimately stored in data structure 610 of the patient's record 46 so that the patient's physician can review the profile in subsequent steps.

Steps 516-518. In step 516, the biological specimen and clinical characterization for a given patient are received from an affiliate health care facility. In some embodiments, the biological specimen is sent to a third party testing facility in order to perform molecular profiling. Regardless of whether the molecular profiling is performed, in preferred embodiments at least a portion of the biological sample is sent to the central health care facility for permanent storage and reference. The type of molecular profile obtained in the embodiment illustrated in FIG. 5 can be any of the molecular profiles described in previous sections, including molecular profiles 50 (FIG. 1). The clinical characterization and molecular profile for the patient under examination in steps 510 through 514 is stored is stored in the patient record 46 associated with the patient. In preferred embodiments, computer 10*b* stores or has access to the patient record 46 for each patient enrolled in a given health care program so that the data can be used to refine treatment regimens 620 elucidated in steps 502 through 506, as disclosed in more detail in step 526, below.

Step 520. The molecular profile and clinical characterization are used as a basis for selecting one or more treatment regimens 620. Therapeutic determination module 620 includes instructions for identifying one or more treatment regimen, from among the plurality of treatment regimens stored in compute 10*b*, for the patient. Module 78 performs this task by matching the molecular profile and the clinical characterization of the patient to the selection criteria 622 of each treatment regimen 620. Selection criteria 622 are discussed in step 506, above. One or more matching treatment regimens are sent from computer 10*b* to computer 10*a* where they are received and stored by treatment regimen module 82. In some embodiments, treatment regimen module is simply a web browser (e.g., Internet Explorer, Microsoft, Redmond, Wash.) that has been instructed to review select treatment regimens stored on computer 10*b*.

Step 522. In step 522, an attending medical practitioner (e.g., the patient's primary physician) selects one of the treatment regimens 620 that was identified by therapeutic determination module 78.

Step 524. In step 524, the clinical outcome of the patient is monitored. In some embodiments, step 524 encompasses steps 214-220 of FIG. 20 in which, at each time interval t, the clinical outcome of the patient is monitored by making a new clinical assessment of the patient, optionally obtaining and molecular-profiling a patient biological specimen, and requesting updated guidance from therapeutic determination module 78 on appropriate treatment regimens.

Step 526. In step 516, the clinical outcome of the patient under study is used as a basis for refining the treatment regimens relating to the disease that the patient had. More typically, the patients clinical outcome is combined with the clinical outcome of other patients having the same disease as the patient. These outcomes are correlated with the molecular profiles and other clinical characteristics of the patients to determine new correlations and relationships and to test the assumptions relied upon in the initial development of the clinical trials. For example, consider the case in which the disease under study is colon cancer and that the treatment regimens 620 relied upon to treat patients with colon cancer is to use osteopontin levels as a basis for predicting colon cancer severity and for selecting the aggressiveness of the colon cancer treatment. In step 526, the historical longitudinal data from successive instances of step 524, where each instance of step 524 represents a different patient, can be used to verify that osteopontin levels are an accurate indicator of colon cancer severity and that such levels provide a sound basis for deciding which treatment regimen to follow for a given patient.

Step 528. In step 528, the refined treatment regimens of step 526 are used as the basis for hypothesis for subsequent clinical trials. Thus, it can be seen that the process flow illustrated in FIG. 5 represents a repeating cycle in which the results of clinical trials or peer reviewed journal articles are used to develop treatment regimens, the success of these treatment regimens is judged using a consenting patient population. The clinical outcome of the patient population is used as the basis for new clinical trials thereby completing the cycle.

5. Medical Cards

Another aspect of the invention is a medical card defined by a base constructed from a substantially flat piece of plastic having a first face and second face, at least one of the first face and the second face comprising indicia placed thereon, the indicia comprising (i) an identification of a patient uniquely associated with the medical card and (ii) a magnetic strip bearing electronic information. The electronic information comprises (i) an identification of the patient, a diagnosis of the patient, and (iii) an identification of a doctor that made the diagnosis. In some embodiments, the electronic information in the magnetic strip further comprises at least one demographic characteristic describing the patient. Such demographic characteristics can be, for example, any of the characteristics illustrated in FIG. 4. In some embodiments, the electronic information further comprises an analysis of a molecular profile 50 from a biological specimen obtained from the patient. In some embodiments, the electronic information further comprises a clinical characterization 52 of the patient. In some embodiments, the diagnosis is that the patient has a disease such as a type of cancer, a heart disease, an autoimmune disease, a neurodegenerative disorder, an infectious disease and/or any of the diseases described in Section 5.10, below.

In some embodiments, the medical card further comprises an identification of a treatment regimen 620 that has been assigned to the patient. In some embodiments, the electronic information stored in the magnetic strip of the card includes a clinical characterization 52 that comprises a clinical diagnosis having an ICD-9 code and a date the clinical diagnosis was made for the patient. In some embodiments, the electronic information further comprises an objective progress assessment for the patient or a subjective progress assessment for the patient. In some embodiments, the electronic information further comprises a Current Procedural Terminology (CPT) code for a procedure performed on the patient and a date the procedure was performed on the patient. In still other embodiments, the electronic information further comprises a detail about a drug prescribed to the patient. For example, the detail about the drug can include at least one of a name of the drug prescribed, a strength of the drug prescribed, a quantity of the drug prescribed, and a number of refills of the drug prescribed.

6. Exemplary Normalization Routines

A number of different normalization protocols can be used to normalize cellular constituent abundance data. Some such normalization protocols are described in this section. Typically, the normalization comprises normalizing the expression level measurement of each gene in a plurality of genes that is expressed by patient. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij}=(I_{ij}-mnI_i)/sdI_i,$$

and $$Zdiff_j(x,y)=Z\text{-score}_{xj}-Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij}=(I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij}=\log(1.0+(I_{ij}/\text{median}I_i)).$$

Yet another normalization protocol is the Z-score standard deviation log of intensity protocol. In this protocol, raw expression intensities are normalized by the mean log intensity ($mnLI_i$) and standard deviation log intensity ($sdLI_i$). For microarray data, the mean log intensity and the standard deviation log intensity is computed for the log of raw intensity of control genes. Then, the Z-score intensity $Z \log S_{ij}$ for probe i and spot j is:

$$Z \log S_{ij}=(\log(I_{ij})-mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)-mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity $Z\log A_{ij}$ for probe i and spot j is:

$$Z \log A_{ij}=(\log(I_{ij})-mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. See, for example, section 5.8.1.5. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

7. Analytic Kit Implementation

In one embodiment, the methods of this invention can be implemented by use of kits. Such kits contain microarrays, such as those described in Subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more databases described above and in FIGS. 1, 6, and 7, encoded on computer readable medium, and/or an access authorization to use the databases described above from a remote networked computer.

In another preferred embodiment, a kit of the invention further contains software capable of being loaded into the memory of a computer system such as the one described supra, and illustrated in FIG. 1 and/or FIG. 7. The software contained in the kit of this invention, is essentially identical to the software described above in conjunction with FIG. 1 and/or FIG. 7.

Alternative kits for implementing the analytic methods of this invention will be apparent to one of skill in the art and are intended to be comprehended within the accompanying claims.

8. Transcriptional State Measurements

This section provides some exemplary methods for measuring the expression level of genes, which are one type of cellular constituent. One of skill in the art will appreciate that this invention is not limited to the following specific methods for measuring the expression level of genes in each organism in a plurality of organisms.

8.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance ratios. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, a molecular profile 50 is an expression profile that is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 $cm^2$ and 25 $cm^2$, preferably 1 to 3 $cm^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

In some embodiments, the microarray is a first edition Human HuFL6800 (6800 elements) or a second edition HuU95A (12,000 elements) GeneChip. The HuFL6800 chip contains probes corresponding to 5000 named genes (based on the National Center for Biotechnology Information UniGene Build 139, as provided by Affymetrix, Santa Clara, Calif.), whereas the HuU95A contains more than 12,000 probe sets corresponding to 8900 names genes (UniGene Build 139).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (e.g., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence can also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene or exon. However, if desired, the profiling arrays can contain at least 2, 5, 10, 100, or 1000 or more probes specific to some target genes or exons. For example, the array can contain probes tiled across the sequence of the longest mRNA isoform of a gene at single base steps.

In specific embodiments of the invention, when an exon has alternative spliced variants, a set of polynucleotide probes of successive overlapping sequences, e.g., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the exon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such instances, an exon is represented by a single binding site on the profiling arrays. In some preferred cases, an exon is represented by one or more binding sites on the profiling arrays, each of the binding sites comprising a probe with a polynucleotide sequence that is complementary to an RNA fragment that is a substantial portion of the target exon. The lengths of such probes are normally between 15-600 bases, preferably between 20-200 bases, more preferably between 30-100 bases, and most preferably between 40-80 bases. The average length of an exon is about 200 bases in some embodiments of the present invention (see, e.g., Lewin, Genes V, Oxford University Press, Oxford, 1994). A probe of length of 40-80 allows more specific binding of the exon than a probe of shorter length, thereby increasing the specificity of the probe to the target exon. For certain genes, one or more targeted exons can have sequence lengths less than 40-80 bases. In such cases, if probes with sequences longer than the target exons are to be used, it can be desirable to design probes comprising sequences that include the entire target exon flanked by sequences from the adjacent constitutively splice exon or exons such that the probe sequences are complementary to the corresponding sequence segments in the mRNAs. Using flanking sequences from adjacent constitutively spliced exon or exons rather than the genomic flanking sequences, e.g., intron sequences, permits comparable hybridization stringency with other probes of the same length. Preferably, the flanking sequences used are from the adjacent constitutively spliced exon or exons that are not involved in any alternative pathways. More preferably, the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon can be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (e.g., probes) for sets of exons for one or more genes relevant to the action of a drug of interest or in a biological pathway of interest. As discussed above, a "gene" is identified as a portion of DNA that is transcribed by RNA polymerase, which may include a 5N untranslated region ("UTR"), introns, exons and a 3N UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer than 99 amino acid residues in length. Analysis of these ORFs indicates that there are 5,885 ORFs that are likely to encode protein products (Goffeau et al., 1996, *Science* 274:546-567). In preferred embodiments of the invention, an array set comprising, in total, probes for all known or predicted exons in the genome of an organism are provided. As a non-limiting example, the present invention provides an array set comprising one or two probes for all or a portion of the known exons in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Schena et al., 1995, Quantitative monitoring of gene expression patterns with a complementary DNA microarray, *Science* 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, Texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at 2, 4, 6, 10, 12, 16, 18, 48 or 72 times as long as the first hybridization time.

8.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than 40 bases in length. Alternatively, when a large set of redundant probes is to be used for an exon, the probes normally comprise nucleotide sequences of 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; and U.S. Pat. No. 5,539,083).

In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209).

8.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3N end of the polynucleotide. Alternatively, polynucleotide probes can be attached to the surface covalently at the 5N end of the polynucleotide (see for example, Blanchard, 1998, in *Synthetic DNA Arrays in Genetic Engineering*, Vol. 20, J. K. Setlow, Ed., Plenum Press, New York at pages 111-123).

8.1.3. Target Polynucleotide Molecules

Target polynucleotides that can be analyzed by the methods and compositions of the invention include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides that can also be analyzed by the methods of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules can be naturally occurring nucleic acid molecules such as genomic or extragenomic DNA molecules isolated from a patient, or RNA molecules, such as mRNA molecules, isolated from a patient. Alternatively, the polynucleotide molecules can be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, the target polynucleotides can correspond to particular fragments of a gene transcript. For example, the target polynucleotides may correspond to different exons of the same gene, e.g., so that different splice variants of the gene can be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules that are representative of the original nucleic acid population of the cell.

The target polynucleotides to be analyzed by the methods of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, $^{15}N$ and $^{125}I$. Fluorescent molecules suitable for the present invention include, but are not limited to, fluorescein and its derivatives, rhodamine and its derivatives, Texas red, 5Ncarboxy-fluorescein ("FMA"), 2N,7N-dimethoxy-4N,5N-dichloro-6-carboxy-fluorescein ("JOE"), N,N,NN,NN-tetramethyl-6-carboxy-rhodamine ("TAMRA"), 6Ncarboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

8.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (e.g., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

8.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Schena et al., 1995, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Res. 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Shalon et al., 1996, Genome Res. 6:639-645. Alternatively, the fiber-optic bundle described by Ferguson et al., 1996, Nature Biotech. 14:1681-1684, can be used to monitor mRNA abundance levels at a large number of sites simultaneously.

Signals are recorded and, in a preferred embodiment, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (e.g., the abundance is different in the two sources of mRNA tested) or as not perturbed (e.g., the relative abundance is the same). As used herein, a difference between the two sources of RNA of at least a factor of 25% (e.g., RNA is 25% more abundant in one source than in the other source), more usually 50%, even more often by a factor of 2 (e.g., twice as abundant), 3 (three times as abundant), or 5 (five times as abundant) is scored as a perturbation. Present detection methods allow reliable detection of differences of an order of 1.5 fold to 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

8.2. Other Methods of Transcriptional State Measurement

The transcriptional state of cellular constituent in a biological specimen can be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, Science 270: 484-487).

9. Measurement of Other Aspects of the Biological State

In various embodiments of the present invention, aspects of the biological state other than the transcriptional state, such as the translational state, the activity state, or mixed aspects can be measured. Thus, in such embodiments, cellular constituent data used in molecular profile 50 can include translational state measurements or even protein expression measurements. Details of embodiments in which aspects of the biological state other than the transcriptional state are described in this section.

9.1. Translational State Measurements

Measurement of the translational state can be performed according to several methods. For example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, Antibodies: A Laboratory Manual, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274: 536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

9.2. Other Types of Cellular Constituent Abundance Measurements

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plate, in which each well contains its own unique chemistry is provided. Each unique chemistry is designed to test a particular phenotype. Cells from the organism of interest are pipetted into each well. If the cells exhibits the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, p. 1246.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from a biological specimen obtained from the patient are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, 1246-55.

In some embodiments of the present invention, the cellular constituents that are measured are metabolites. Metabolites include, but are not limited to, amino acids, metals, soluble sugars, sugar phosphates, and complex carbohydrates. Such metabolites can be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), Fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, In: *Modern techniques for rapid microbiological analysis*, 43-96, Nelson, W. H., ed., VCH Publishers, New York), Raman spectrometry, gas chromatography-mass spectroscopy (GC-MS) (Fiehn et al., 2000, Nature Biotechnology 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods can be combined with established chemometric methods that make use of artificial neural networks and genetic programming in order to discriminate between closely related samples.

10. Exemplary Diseases

As discussed supra, the present invention provides an method for treating patients that have a disease. Exemplary diseases that can be treated include asthma, cancers, common late-onset Alzheimer's disease, diabetes, heart disease, hereditary early-onset Alzheimer's disease (George-Hyslop et al., 1990, *Nature* 347:194), hereditary nonpolyposis colon cancer, hypertension, infection, maturity-onset diabetes of the young (Barbosa et al., 1976, *Diabete Metab.* 2:160), mellitus, nonalcoholic fatty liver (NAFL) (Younossi, et al., 2002, Hepatology 35, 746-752), nonalcoholic steatohepatitis (NASH) (James & Day, 1998, *J. Hepatol.* 29:495-501), non-insulin-dependent diabetes mellitus, and polycystic kidney disease (Reeders et al., 1987, *Human Genetics* 76:348).

Cancers that can be treated in accordance with the present invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

11. Exemplary Database Architectures

In some embodiments, patient database 44 and/or clinical research repository 84 (FIGS. 1, 6, and 7) is a data warehouse. Data warehouses are typically structured as either relational databases or multidimensional data cubes. In this section, exemplary databases 44 and/or clinical research repository 84 having a relational database or a multidimensional data cube architecture are described. For more information on relational databases and multidimensional data cubes, see Berson and Smith, 1997, *Data Warehousing, Data Mining and OLAP*, McGraw-Hill, New York; Freeze, 2000, *Unlocking OLAP with Microsoft SQL Server and Excel* 2000, IDG Books Worldwide, Inc., Foster City, Calif.; and Thomson, 1997, *OLAP Solutions: Building Multidimensional Information Systems*, Wiley Computer Publishing, New York. In addition, it will be appreciated that, in some embodiments, database 44 and/or clinical research repository 84 does not have a formal hierarchical structure.

11.1. Data Organization

Databases have typically been used for operational purposes (OLTP), such as order entry, accounting and inventory control. More recently, corporations and scientific projects have been building databases, called data warehouses or large on-line analytical processing (OLAP) databases, explicitly for the purposes of exploration and analysis. The "data warehouse" can be described as a subject-oriented, integrated, time-variant, nonvolatile collection of data in support of management decisions. Data warehouses are built using both relational databases and specialized multidimensional structures called data cubes. In some embodiments database 44 and/or clinical research repository 84 is a datacube or a relational database.

11.2. Relational Databases

Relational databases organize data into tables where each row corresponds to a basic entity or fact and each column represents a property of that entity. For example, a table can represent transactions in a bank, where each row corresponds to a single transaction, and each transaction has multiple attributes, such as the transaction amount, the account balance, the bank branch, and the customer. The relational table is referred to as a relation, a row as a tuple, and a column as an attribute or field. The attributes within a relation can be partitioned into two types: dimensions and measures. Dimensions and measures are similar to independent and dependent variables in traditional analysis. For example, the bank branch and the customer would be dimensions, while the account balance would be a measure. A single relational database will often describe many heterogeneous but interrelated entities. For example, a database designed for a restaurant chain might maintain information about employees, products, and sales. The database schema defines the relations in a database, the relationships between those relations, and how the relations model the entities of interest.

11.3. Data Cubes

A data warehouse can be constructed as a relational database using either a star or snowflake schema and will provide a conceptual model of a multidimensional data set.

Each axis in the corresponding data cube represents a dimension in a relational schema and consists of every possible value for that dimension. For example, an axis corresponding to states would have fifty values, one for each state. Each cell in the data cube corresponds to a unique combination of values for the dimensions. For example, if there are two dimensions, "State" and "Product," then there would be a cell for every unique combination of the two, e.g., one cell each for (California, Tea), (California, Coffee), (Florida, Tea), (Florida, Coffee), etc. Each cell contains one value per measure of the data cube. So if product production and consumption information is needed, then each cell would contain two values, one for the number of products of each type consumed in that state, and one for the number of products of each type produced in that state. Dimensions within a data warehouse are often augmented with a hierarchical structure. If each dimension has a hierarchical structure, then the data warehouse is not a single data cube but rather a lattice of data cubes.

Examples

Computer systems, computer program products, methods, and kits for providing health care have been disclosed. What follows are select examples that illustrate the utility and value of the present invention.

1. Commercialization Potential

An outcome from the novel approaches described in Section 5 may be several potential services and products that have a commercial value connected to them. The following is a summary of those product and service opportunities both short and long-term that result from such methods:

I. A longitudinal database with information on patients including tissue and blood sample information. The containment of these specimens will facilitate the determination of better treatment and prevention. Such a database could be commercialized by transactions with a number of constituents including pharmaceutical companies, diagnostic companies, payers, healthcare providers, and other research centers.

II. Evidence-based guidelines, which describe the best treatment options based on specific information about patient medical histories and their tumors.

III. Identification and confirmation of biomarkers as drug targets and the analysis of the efficacy of existing therapies developed from the plethora of information, which could be commercialized by transactions with life science companies or spun-off as new companies.

IV. Diagnostics developed from the data and human samples that could be commercialized by transactions with diagnostic companies or spun-off as new companies.

Short-Term. The commercial potential of a longitudinal database is evident in several recent transactions. For example, deCode and Merck have consummated a deal that is predicated on the population genetics information deCode has gathered from their longitudinal studies. Additionally, venture capitalists have invested in genomics companies who have similar longitudinal databases. The value of such databases will be a function of the application of the data to develop products and services. Methodologies exist to calculate such value. However, assessing the value is more nebulous than drug target deals. The value may be predicated on a "cost approach," e.g., what the buyer would have to do to recreate the data plus some additional value for analysis less any obsolete costs of the data. Ultimately, the question of value lies with the buyer and what they ultimately gain from the information.

One of the potential valuable benefits of the systems and methods of the present invention is the development of improved clinical practice guidelines. Clinical practice consensus guidelines are available through the NCCN website as well as other cancer websites. These guidelines are based on the consensus of practice and are not necessarily evidence-based. Though evidence-based studies do exist for certain disease sites, they continue to evolve as genomics and proteomics develop. The systems and methods of the present invention can be used to provide evidence-based guidelines to affiliates as part of their participation in the health care plans of the present invention.

Long-Term. The data that results from the longitudinal information that the systems and methods of the present invention will collect, the discoveries that may occur through large-scale gene expression and protein analysis, and the tumor banking activities of TCC may yield insights into new drug targets, therapies and diagnostics as the processes illustrated in FIGS. 2, 5, and 9 progress over time. For example, new biomarkers may be discovered that assist in diagnosing the presence of cancer in a patient and how the patient is responding to therapies. Extensive gene expression and proteomics analysis may produce new drug targets and/or insights into how existing therapies can be administered or modified.

2. Affiliate Network

An affiliate network is important to the success of some embodiments of the present invention such as the method disclosed in FIG. 5. Not all patients have the benefit of being treated at central health care facility for a several reasons, including distance, lack of healthcare coverage, and situations in which the care at the central health care facility is not covered by all third-party providers. To bring the benefits of health care treatment in accordance with the present invention to the broadest section of residents in a given geographical region, a central health care facility preferably has an affiliate network. This affiliate network provides a foundation upon which to launch a health care plan in accordance with the present invention and ensures that the plan is sustainable. In such a plan, the central health care facility ensure that the affiliate network is a true "partner" in the development and implementation of the health care plan by actively enrolling a significant portion of the affiliate patients in clinical trials run by the central health care facility and by providing continual updates of their prognosis.

REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1 and/or FIG. 7 and/or FIG. 9. These program modules may be stored on a CD-ROM, DVD, magnetic disk storage product, or any other computer readable data or program storage product. The software modules in the computer program product can also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A system for managing patient data comprising:
   a computing system including a processing unit and a storage, the processing unit executing one or more programs for managing patient data, where managing patient data includes
   enrolling patients in a centralized care network including presenting each patient with an electronic enrollment interface, assigning each patient a patient identifier, and receiving an electronic consent to collect data;
   providing patient data to the centralized care network including patient data relating to disease progression, clinical trials and treatments rendered;
   receiving a treatment regimen, from among a plurality of treatment regimens available to treat a given patient, the treatment regimen based at least in part on the patient data including a molecular profile, a current clinical characterization of the patient and evidence based data;
   processing the received treatment regimen including monitoring clinical outcome of the given patient after application of the treatment regimen, and based at least in part on the clinical outcome, enabling an update to the treatment regimen including providing clinical outcome data to the centralized care network; and
   receiving an updated treatment regimen, from among a plurality of treatment regimens available to treat a given patient, the updated treatment regimen based at least in part on the patient data including a molecular profile, a current clinical characterization of the patient, evidence based data and the clinical outcome data.

2. The system of claim 1 where the centralized care network is coupled to a plurality of affiliate computing systems, each affiliate computing system presenting the electronic enrollment interface to a respective patient that is to be enrolled from the affiliate computing system.

3. The system of claim 2 where providing patient data includes providing patient data from the affiliate computing system.

4. The system of claim 1 where providing patient data includes providing clinical trial information including information related to clinical trials a patient has entered, a treatment protocol for the respective clinical trial, and clinical assessment data related to progress of the patient in the respective clinical trial.

5. The system of claim 1 where the program for managing patient data includes a user interface for facilitating enrollment of patients at a remote facility and supplemental information provisioning from the remote facility.

6. The system of claim 1 where the program for managing patient data includes providing a user interface for presenting treatment information including one or more treatment recommendations, patient profiles or disease profiles to a patient or a patient care giver, the treatment information having been provided by the centralized care network.

7. A computer network comprising:
   a plurality of affiliate computing systems, each affiliate computing system including a processing unit and storage, the processing unit executing one or more programs for supporting care of a patient, where supporting includes
   enrolling patients in a centralized network including presenting an interface to the patient for receiving patient data;

managing patient data including providing an interface to a care giver for providing additional patient data relating to one or more of disease progression, clinical trials or treatments rendered;

providing patient data to the centralized network; and the centralized network including a central computing system, the central computing system being coupled to each affiliate computing system by way of a network, the central computing system including a processing unit and storage, the processing unit executing one or more programs for managing patient records stored in the storage, where managing patient records includes presenting an interface to an affiliate computing system for presenting one or more treatment regimens, from among a plurality of treatment regimens available for treating a given patient, the treatment regimens based at least in part on a molecular profile, the current clinical characterization of the given patient and the evidence based data; and wherein each affiliate computing system is operable to receive treatment regimens and process a received treatment regimen including monitoring clinical outcome of the given patient after application of the treatment regimen, and based at least in part on the clinical outcome, enabling an update to the treatment regimen including providing clinical outcome data to the centralized network; and receiving an updated treatment regimen, from among a plurality of treatment regimens available to treat a given patient, the updated treatment regimen based at least in part on the patient data including a molecular profile, a current clinical characterization of the patient, evidence based data and the clinical outcome data.

8. A computer network comprising:

a plurality of affiliate computing systems, each affiliate computing system including a processing unit and storage, the processing unit executing one or more programs for supporting care of a patient, where supporting includes enrolling patients in a centralized care network including assigning each patient a patient identifier, and receiving consent to collect data; and providing patient data to the centralized care network including patient data relating to one or more of disease progression, clinical trials or treatments rendered; and the centralized care network including a central health care computing system, the central health care computing system being coupled to each affiliate computing system by way of a network, the central health care computing system including a processing unit and storage, the processing unit executing one or more programs for managing patient records stored in the storage, where managing patient records includes receiving patient data from an affiliate computing system including new data for new patients and updated patient data reflecting new or changing data with respect to an already registered patient;

receiving developed treatment protocols based on longitudinal data derived from the patient data, where the longitudinal data relates to treatments and outcomes; and distributing developed treatment protocols to one or more of the affiliate computing systems for use in treating future patients serviced by a treatment center associated with a given affiliate computing system;

wherein each affiliate computing system is operable to receive treatment regimens and process a received treatment regimen including monitoring clinical outcome of a given patient after application of a treatment protocol, and based at least in part on the clinical outcome, enabling an update to the treatment protocol including providing clinical outcome data to the centralized network; and receiving an updated treatment protocol, from among a plurality of treatment protocols available to treat a given patient, the updated treatment protocol based at least in part on the patient data including a molecular profile, a current clinical characterization of the patient, evidence based data and the clinical outcome data.

* * * * *